United States Patent [19]

Soares et al.

[11] Patent Number: 5,482,845
[45] Date of Patent: Jan. 9, 1996

[54] METHOD FOR CONSTRUCTION OF NORMALIZED CDNA LIBRARIES

[75] Inventors: Marcelo B. Soares, New York, N.Y.; Argiris Efstratiadis, Englewood, N.J.

[73] Assignee: The Trustees of Columbia University in the City of New York, New York, N.Y.

[21] Appl. No.: 126,594

[22] Filed: Sep. 24, 1993

[51] Int. Cl.⁶ .................................................. C12P 19/34
[52] U.S. Cl. .......................... 435/91.1; 435/6; 536/25.4; 935/80
[58] Field of Search ..................... 435/6, 91.1; 536/25.4; 935/80

[56] References Cited

PUBLICATIONS

Ko, M. S. H., (1990) An 'equalized cDNA library' by the reassociation of short double–stranded cDNAs. *Nucleic Acids Research*, vol. 18, No. 19, pp. 5705–5711. (Exhibit B).

Patanjali, S. R., et al. (Mar. 1991) Construction of a uniform–abundance (normalized) cDNA library. *Proc. Natl. Acad. Sci. U.S.A.*, 88:1943–1947. (Exhibit C).

NTIS Progress Report, Soares & Efstratiadis, Oct. 1992.

*Primary Examiner*—Margaret Moskowitz Parr
*Assistant Examiner*—Kenneth R. Horlick
*Attorney, Agent, or Firm*—John P. White

[57] ABSTRACT

This invention provides a method to normalize a directional cDNA library constructed in a vector that allows propagation in single-stranded circle form comprising: (a) propagating the directional cDNA library in single-stranded circles; (b) generating fragments complementary to the 3' noncoding sequence of the single-stranded circles in the library to produce partial duplexes; (c) purifying the partial duplexes; (d) melting and reassociating the purified partial duplexes to moderate Cot; and (e) purifying the unassociated single-stranded circles, thereby generating a normalized cDNA library.

8 Claims, 4 Drawing Sheets cDNA LIBRARY NORMALIZATION

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GCGGCCGC    8

( 2 ) INFORMATION FOR SEQ ID NO:2:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

AAUAAA    6

( 2 ) INFORMATION FOR SEQ ID NO:3:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GGCCCTCGAG GCCAAGAATT CCCGACTACG TAGTCGGGGA TCCGTCTTAA TTAAGCGGCC    60

GCAAGCTT    68

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

AACTGGAAGA ATTCGCGGCC GCAGGAA    27

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

GGCCGCAGGA A    11

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GGCCGCAGGA AT    12

( 2 ) INFORMATION FOR SEQ ID NO:7:

( i ) SEQUENCE CHARACTERISTICS:
            ( A ) LENGTH: 8 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

TTAATTAA                                                                                                             8

( 2 ) INFORMATION FOR SEQ ID NO:8:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

TTTTTTTAA TTAATTTTTT TTTTTTTTTT TT                                           32

( 2 ) INFORMATION FOR SEQ ID NO:9:

( i ) SEQUENCE CHARACTERISTICS:
            ( A ) LENGTH: 35 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

TTTTTTTAA TTAAGAGTTT TTTTTTTTTT TTTTT                                    35

( 2 ) INFORMATION FOR SEQ ID NO:10:

( i ) SEQUENCE CHARACTERISTICS:
            ( A ) LENGTH: 35 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

TTTTTTTAA TTAATAGGTT TTTTTTTTTT TTTTT                                    35

( 2 ) INFORMATION FOR SEQ ID NO:11:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

TTTTTTTTAA TTAACGTCTT TTTTTTTTT TTTTT         35

( 2 ) INFORMATION FOR SEQ ID NO:12:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

TTTTTTTTAA TTAATGCTTT TTTTTTTTT TTTTT         35

( 2 ) INFORMATION FOR SEQ ID NO:13:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

TTTTTTTTAA TTAAAGCATT TTTTTTTTT TTTTT         35

( 2 ) INFORMATION FOR SEQ ID NO:14:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

TTTTTTTTAA TTAAGCTATT TTTTTTTTT TTTTT         35

( 2 ) INFORMATION FOR SEQ ID NO:15:

( i ) SEQUENCE CHARACTERISTICS:
      ( A ) LENGTH: 35 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

TTTTTTTTAA TTAACAATTT TTTTTTTTT TTTTT                    35

(2) INFORMATION FOR SEQ ID NO:16:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

TTTTTTTTAA TTAACTGATT TTTTTTTTT TTTTT                    35

(2) INFORMATION FOR SEQ ID NO:17:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

TTTTTTTTAA TTAAAAAGTT TTTTTTTTT TTTTT                    35

(2) INFORMATION FOR SEQ ID NO:18:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

TTTTTTTTAA TTAAACTGTT TTTTTTTTT TTTTT                    35

(2) INFORMATION FOR SEQ ID NO:19:

(i) SEQUENCE CHARACTERISTICS:
(A) LENGTH: 35 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:19:

TTTTTTTTAA TTAAATCCTT TTTTTTTTT TTTTT    35

(2) INFORMATION FOR SEQ ID NO:20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:20:

TTTTTTTTAA TTAACCACTT TTTTTTTTT TTTTT    35

(2) INFORMATION FOR SEQ ID NO:21:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:21:

TTTTTTTTAA TTAAGGAATT TTTTTTTTT TTTTT    35

(2) INFORMATION FOR SEQ ID NO:22:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:22:

GCGGCCTC    8

(2) INFORMATION FOR SEQ ID NO:23:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (i i) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

TTAATTAA                                                                                                    8

( 2 ) INFORMATION FOR SEQ ID NO:24:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

CCGCTTAATT AANNNN                                                                                           16

( 2 ) INFORMATION FOR SEQ ID NO:25:

( i ) SEQUENCE CHARACTERISTICS:
                ( A ) LENGTH: 4 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

CCGC                                                                                                        4

( 2 ) INFORMATION FOR SEQ ID NO:26:

( i ) SEQUENCE CHARACTERISTICS:
                ( A ) LENGTH: 29 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

NNNNTTAATT AAGCGGCCGC AAGCTTATT                                                                             29

METHOD FOR CONSTRUCTION OF NORMALIZED CDNA LIBRARIES

This invention was made with support under Grant Number DE-FG0291ER61233 from the U.S. Department of Energy. Accordingly, the U.S. Government has certain rights in the invention.

BACKGROUND

Significance of cDNA library normalization

A typical somatic cell contains approximately 0.6 pg of mRNA. Thus, there are about 500,000 mRNA molecules per cell assuming that the average size of a mRNA is 2 kb ($11 \times 10^{-7}$ pg). These mRNAs occur in three frequency classes (reviewed by Davidson and Britten, 1979):

|  | % mass | # mRNA species | # copies per species | Total mRNAs |
|---|---|---|---|---|
| Superprevalent | 10 (10–20) | 10 | 5,000 | 50,000 |
| Moderately Prevalent | 45 (40–45) | 1,000 | 225 | 225,000 |
| Complex | 45 (40–45) | 15,000 | 15 | 225,000 |

Accordingly, the rarest mRNA (1 copy per cell) will be present at a frequency of 1/500,000. Its representation in a cDNA library will depend on the number of independent recombinants. The probability that a given mRNA will be represented can be expressed by the equation $P(x)=1-(1-f)^n$, where f-frequency (1/500,000) and n-number of recombinant clones. Therefore, the probability that the most rare mRNA will not be represented in a cDNA library of $10^7$ recombinants is $2 \times 10^{-9}$.

Although even the rarest mRNA will be represented in a library, its identification is very difficult (1/500,000). In a normalized cDNA library, however, the frequency of each clone is in the same narrow range and depends on the complexity of the library.

Assuming that there are 50,000 to 100,000 genes in the human genome (Bishop et al., 1974), an ideal normalized cDNA library from a great variety of tissues containing 1–2 kb cloned inserts of every single expressed human gene would have a complexity of 50,000 to 200,000 kb, and every clone would be represented at a frequency of 1/50,000 to 1/100,000, which would still be 5–10 times higher than the frequency of the most rare mRNA in a single somatic cell (1/500,000).

According to the considerations described above, the relative frequency of a member of each class of sequences (superprevalent, moderately prevalent and complex) in a representative cDNA library of a typical cell is I:II:III=1.7 and III=25. At Cot=250 (which is 10×the $Cot_{1/2}$ of class III) of the leftover of each component, expressed as % of the initial amount, will be I=0.03%, II=0.6% and III=9%, while the relative average frequency of a member of each class will be 1:1:1, i.e., the library will be normalized.

Methods to normalize cDNA libraries

Thus far, two approaches have been proposed to obtain normalized cDNA libraries (Weissman, 1987). One approach is based on hybridization to genomic DNA. The frequency of each hybridized cDNA in the resulting normalized library would be proportional to that of each corresponding gene in the genomic DNA. The other is a kinetic approach. If cDNA reannealing follows second-order kinetics, rarer species anneal less rapidly and the remaining single-stranded fraction of cDNA becomes progressively more normalized during the course of the hybridization (Galau, et al., 1977). Specific loss of any species of cDNA, regardless of its abundance, does not occur at any Cot value.

Two groups have pursued independently the construction of normalized cDNA libraries based on the kinetic approach (Ko, 1990; Patanjali et al., 1991).

Ko (1990) reported the construction of a normalized mouse cDNA library by a complex scheme involving: a) ligation of cDNAs to a linker-primer adapter; b) three rounds of PCR amplification, denaturation-reassociation, and purification of single-stranded cDNAs by hydroxyapatite (HAP) column chromatography; and c) digestion of the end product using a site present in the linker-primer sequence and cloning (#' non-coding cDNA fragments only) into a plasmid vector.

Colony hybridization with eight probes of different abundances showed a reduction in abundance variation from at least 20,000 fold in the original library to 40-fold in the library constructed after three cycles of normalization.

In Ko's method, both coding and non-coding fragments are present during reassociation. However, after the final digestion and directional cloning steps only the 3' noncoding fragments remain in the normalized library. Ko's rationale for constructing a normalized library consisting exclusively of 3' non-coding sequences was the following. The 3' non-coding terminal exon of a mRNA is almost always unique to that transcript. Thus, during the reassociation step, each 3' non-coding sequence is expected to only reanneal to its very complementary strand. In contrast, coding exons may be conserved among members of a gene family, some of which might be less represented than others in a given tissue. Thus, during reassociation, the most frequent of such coding sequences might cross-hybridize to a related, but divergent, complementary strand from a less prevalent family member, which could result in the elimination of the rarer family member from the normalized library.

Patanjali et al. (1991) obtained a normalized library by a similar method which involved: a) cloning of short cDNAs produced by random priming into λgt10; b) PCR amplification of cloned DNAs; c) denaturation and reassociation to moderate Cot; d) separation of single-strands by HAP chromatography; e) PCR amplification of HAP-flow-through single-stranded cDNAs; and f) cloning into λgt10.

Patanjali's normalized library consisted of cDNA clones containing both coding and non-coding information. However, the cDNAs had to be relatively short and homogenous in length to assure equal efficiency of amplification during the polymerase chain reactions. The potential problem mentioned above of losing sequence representation of rare gene family members in the normalized library was not addressed in Patanjali's approach.

SUMMARY OF THE INVENTION

This invention provides a method to normalize a directional cDNA library constructed in a vector that allows propagation in single-stranded circle form comprising: (a) propagating the directional cDNA library in single-stranded circles; (b) generating fragments complementary to the 3' noncoding sequence of the single-stranded circles in the library to produce partial duplexes; (c) purifying the partial duplexes; (d) melting and reassociating the purified partial duplexes to moderate Cot; and (e) purifying the unassociated single-stranded circles, thereby generating a normalized cDNA library.

This invention also provides a method to normalize a directional cDNA library constructed in a vector that allows propagation in single-stranded circle form comprising: (a) propagating the directional cDNA library in single-stranded circles; (b) generating fragments complementary to the 3' noncoding sequence of the single-stranded circles in the library to produce partial duplexes; (c) purifying the partial duplexes; (d) melting and reassociating the purified partial duplexes to moderate Cot; and (e) purifying the unassociated single-stranded circles, thereby generating a normalized cDNA library, wherein the directional cDNA library is generated by using a primer having a rare restriction enzyme recognition site for the first strand cDNA synthesis, upstream of the oligodT stretch.

This invention further provides normalized libraries generated by the above methods.

The cDNA library in the form of single-stranded circles is annealed to a ½NotI-(dT) oligonucleotide (arrow) and controlled extensions are performed with Klenow in the presence of a 25-fold excess ddNTPs (each A-C-G) over dNTPs (each A-C-G-T). Partially duplex circular molecules are purified from remaining single-stranded circles by hydroxyapatite column chromatography. HAP-bound DNA containing the partially double-stranded circles is melted and re-associated to moderate Cot value. The remaining single-stranded circles (normalized library) are purified from the re-associated material by HAP chromatography, converted to partial duplexes by primed extension and electroporated into competent DH10B bacteria, thus generating a normalized library containing large size cDNA inserts.

Figure 2:
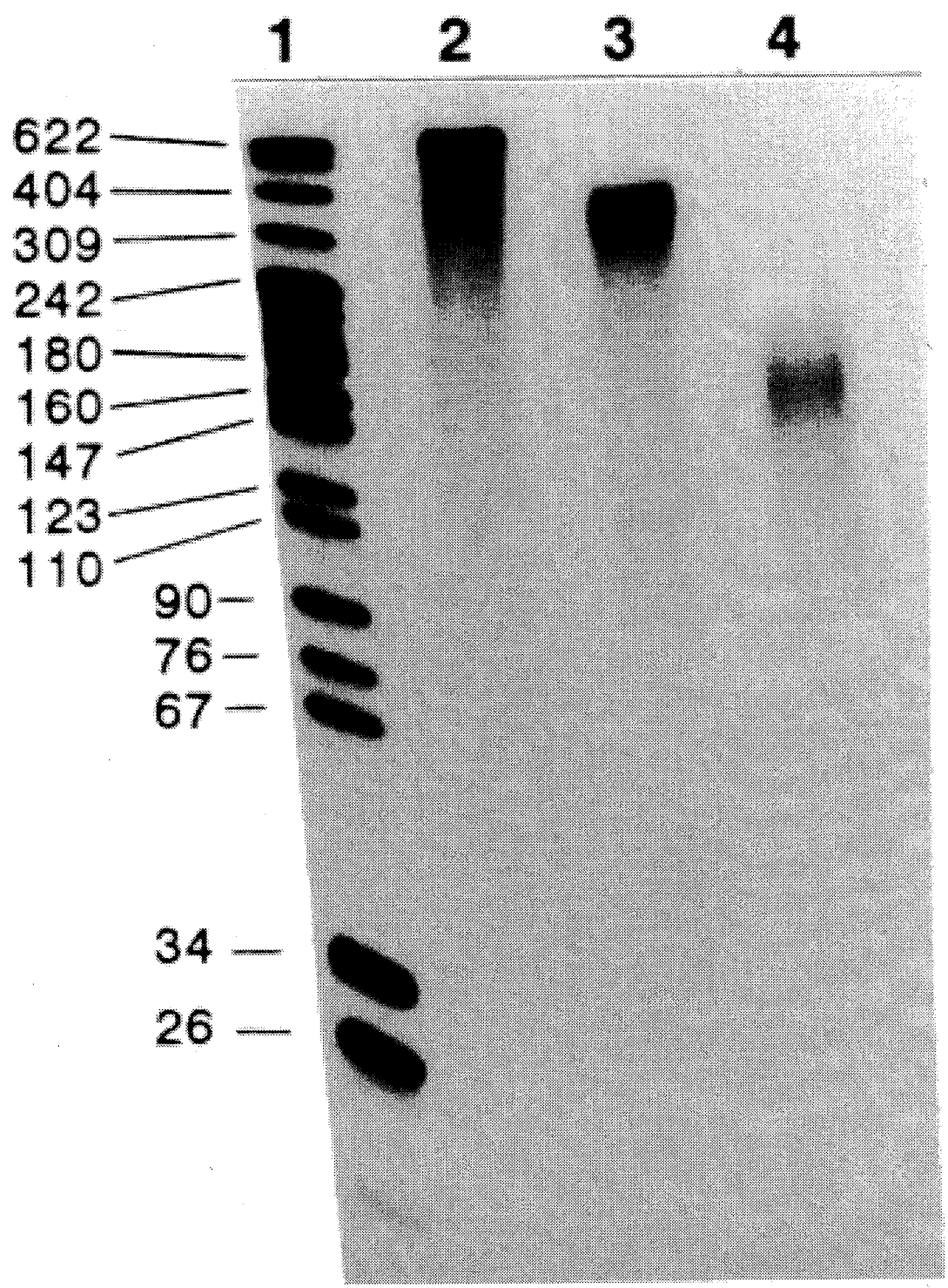

FIG. 2 Controlled Primed Extensions with Klenow Enzyme in the Presence of Different Ratios of dNTPs:ddNTPs.

Controlled primed extention of the single-stranded brain cDNA library with the Klenow enzyme in the presence of a 15-fold, 20-fold or 25-fold excess of ddNTPs (A-G-C) over dNTPs (lanes 2, 3 and 4, respectively). The oligonucleotide utilized as primer was the ½NotI-(dT) 15. Lane 1, pBR322/MspI-digested.

Figure 3:
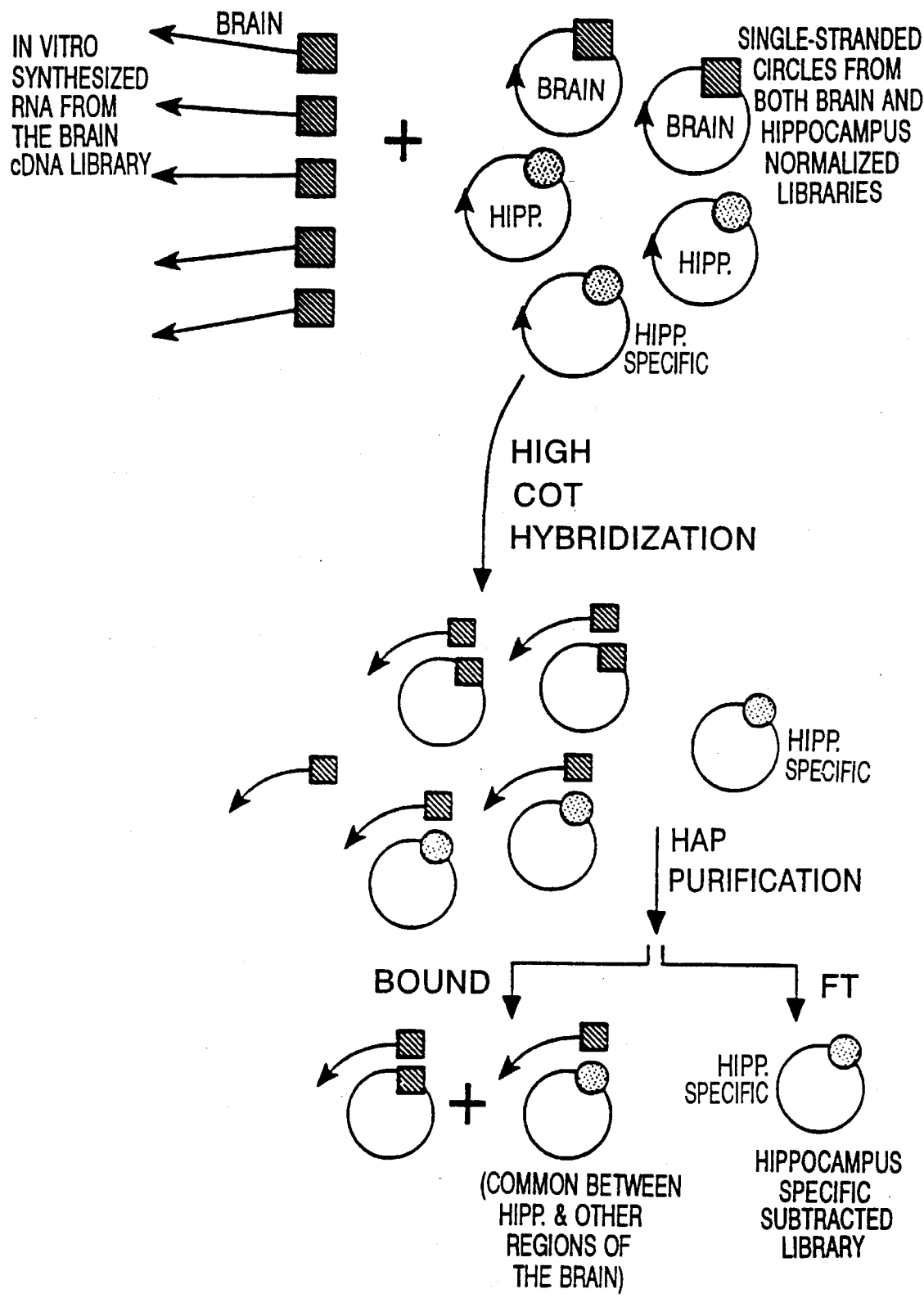

FIG. 3 Model System for Performance of Subtractive Hybridization: Application to the Isolation of Hippocampus-specific cDNAs.

In vitro synthesized RNA from the brain cDNA library (see the text; this library represents all regions of the brain with the exception of hippocampus). Single-stranded circles from both brain and hippocampus normalized libraries (see the text). Hippocampus specific subtracted library.

Figure 4:
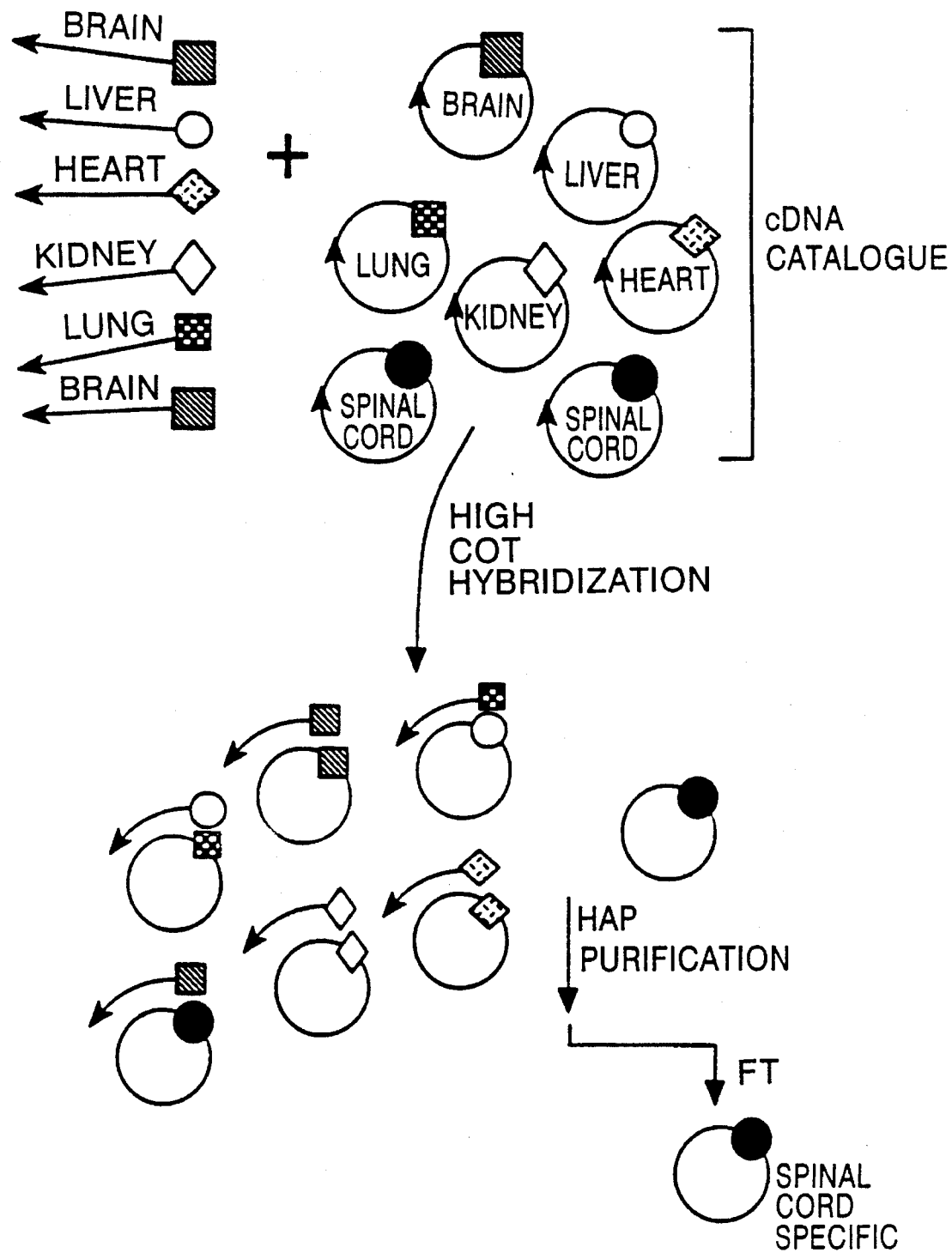

FIG. 4 Substractive hybridizations involving RNA from combinations of normalized libraries and single-stranded circles from the cDNA catalogue. In FIG. 4, a spinal cord-specific library is isolated.

In vitro synthesized RNA from all individual normalized libraries (except spinal cord, in this example) will be hybridized to the cDNA catalogue in the form of single-stranded circles. After purification of the remaining single-stranded circles by HAP chromatography and conversion to partially duplex circular molecules for improvement of electroporation efficiencies, the subtracted library can be propagated in bacteria. All clones from this subtracted library should have the sequence identifier of the spinal cord library.

DETAILED DESCRIPTION OF THE INVENTION

This invention provides a method to normalize a directional cDNA library constructed in a vector that allows propagation in single-stranded circle form comprising: (a) propagating the directional cDNA library in single-stranded circles; (b) generating fragments complementary to the 3' noncoding sequence of the single-stranded circles in the library to produce partial duplexes; (c) purifying the partial duplexes; (d) melting and reassociating the purified partial duplexes to moderate Cot; and (e) purifying the unassociated single-stranded circles, thereby generating a normalized cDNA library.

This invention also provides a method to normalize a directional cDNA library constructed in a vector that allows propagation in single-stranded circle form comprising:(a) propagating the directional cDNA library in single-stranded circles; (b) generating fragments complementary to the 3' noncoding sequence of the single-stranded circles in the library to produce partial duplexes; (c) purifying the partial duplexes; (d) melting and reassociating the purified partial duplexes to moderate Cot; and (e) purifying the unassociated single-stranded circles, thereby generating a normalized cDNA library, wherein the directional cDNA library is generated by using a primer having a rare restriction enzyme recognition site for the first strand cDNA synthesis, upstream of the oligodT stretch.

Vectors that allow propagation in single-stranded circles are well-known in the art. An example of the vector is a phagemid. Another example of the vector is the λzap system.

This invention provides the above method to normalize a cDNA library wherein step (b) the cDNA clones is annealed to an appropriate primer and controlled extensions are performed with an appropriate polymerase in the presence of appropriate ratio between the dideoxynucleotide triphosphates and deoxynucleotide triphosphates.

Rare restriction enzyme recognition sites are well-known in the art. In an embodiment, a Not I site is used. In another embodiment, a Pac I site is used.

In an embodiment, the controlled extensions are performed with Klenow.

In another embodiment, the controlled extensions are performed in the presence of a 25 fold excess of dideoxynucleotide triphosphates containing dideoxyadenosine triphosphate, dideoxycytidine triphosphate and dideoxyguanosine triphosphate over deoxynucleotide triphosphates including deoxyadenosine triphosphate, deoxycytidine triphosphate, deoxyguanosine triphosphate and deoxythymidine triphosphate.

Methods to purify partial duplexes from single-stranded circles have been well-known in the art. In an embodiment, the partial duplexes are purified by hydroxyapatite column chromatography. Other methods such as affinity-capture techniques may be similarly used. One design of the affinity-capture may include using biotinylated deoxynucleotide in the controlled extension reaction and subsequently capture of the incorporated biotinylated nucleotides by avidin conjugated on a column. There are other affinity-capture techniques which may be similarly used in accordance with this invention.

This invention also provides the above methods which further comprise introduction of the unassociated single-stranded circles into host cells. In an embodiment, the single-stranded circles are converted to double-stranded DNA before the introduction into the hosts.

This invention further provides normalized libraries which are generated by the above-described methods.

In an embodiment, the cDNA library is derived from an adult brain. In another embodiment, the cDNA library is derived from an adult hippocampus. In still another embodiment, the cDNA is derived from an infant brain. In another embodiment, the cDNA is derived from a fetal brain. In another embodiment, the cDNA is derived from a fetal liver. In another embodiment, the cDNA is derived from infant liver. In another embodiment, the cDNA is derived from an infant spleen. In still another embodiment, the cDNA is derived from an infant heart. In still another embodiment, the cDNA is derived from an infant lung. In still another embodiment, the cDNA is derived from an infant muscle. In still another embodiment, the cDNA is derived from an adult spinal cord. In a further embodiment, the cDNA is derived from a placenta. In a further embodiment, the cDNA is derived from fetal eyes.

The ultimate goal of this proposal is to generate a reference normalized "human cDNA catalogue", in which the majority of the 100,000 or so existing genes will be represented. It is here referred to as a catalogue because it will comprise a number of different normalized cDNA libraries from a great variety of human tissues and stages of development.

An important feature of this cDNA catalog is that each library component will have a characteristic sequence identifier (tissue-specific IDs), provided by the oligonucleotide primer utilized for first strand cDNA synthesis, the sequence of which will be unique to each library. This cDNA catalogue will be analogous to a folder with many files each of which with a different color.

The next step will be to subdivide the catalogue into a number of normalized sub-libraries according to the pattern of expression of their components. The availability of the cDNA catalogue and of each of the individual normalized libraries will provide a unique opportunity for the performance of a number of subtractive hybridizations for isolation of tissue-specific sublibraries. Most importantly, however, it will allow unambiguous assessment of tissue-specificity by single pass sequencing of randomly picked clones from a subtracted sub-library. This will be possible because in a tissue-specific sublibrary all clones should have the same characteristic sequence ID.

A method to normalize directionally cloned cDNA libraries constructed in phagemid vectors (Soares and Efstratiadis, manuscript in preparation) which presents certain important advantages over other existing protocols (Ko, 1990; Patanjali et al., 1991) has been developed. This method has been utilized to normalize an infant brain cDNA library which has been extensively characterized. This established protocol is used to normalize all libraries that will be constructed.

In summary, this invention has the following specific aims:

a) to construct a number of directionally cloned cDNA libraries from a variety of human tissues and stages of development, each one of which with its unique sequence identifier;

b) to pool all these libraries together and renormalize them to generate the "human cDNA catalogue";

c) to assess the efficiency of normalization by colony hybridization with an already available panel of cDNA probes representing the three frequency classes of mRNAs;

c) to optimize procedures for performance of subtractive hybridization of normalized libraries;

e) to generate a number of tissue-specific normalized sub-libraries by a series of subtractive hybridizations involving each of the individual normalized libraries, or combinations of them, and the cDNA catalogue;

f) to assess the efficacy of each subtractive hybridization by verification that any clone randomly picked from a tissue-specific sub-library has the correct sequence identifier at its 3' end. This will be done by single pass sequencing of a random sampling of clones from each subtracted library; and g) to assess the complexity of each tissue-specific sub-library. In a normalized library the frequency of all clones is within a narrow range. Therefore, by determining the frequency of a few individual clones one can estimate the total number of clones existing in the library.

A different method for normalization of directionally cloned cDNA libraries constructed in phagemid vectors which is based on the same kinetic principle has been developed. Briefly, the method involves annealing of the library in the form of single-stranded circles with a Not I-oligo(dT)18 primer and controlled extensions (160±20 nt) with Klenow in the presence of dNTPs and ddNTPs. After purification of the partial duplexes over HAP, and melting and reannealing to a moderate Cot, unhybridized (normalized) single-stranded circles are purified by HAP and electroporated into bacteria, generating a normalized library. The advantages of this invention can be outlined as follows:

a) because it does not require any cycle of cDNA amplification by the polymerase chain reaction, and therefore no length constraints are imposed, the cDNA clones in the normalized library constructed by this invention have large size inserts (average of 1.7 kb). Because the library is directionally cloned, the 3' end of a clone contains the 3' terminal exon of the mRNA, with a short polyadenylate track and a recognizable polyadenylation signal sequence at the appropriate position, whereas the 5' end of a clone almost always lies within coding sequence;

b) there is no cloning step involved in this invention, after completion of the reassociation reaction; and c) although the normalized library constructed according to this invention consists of clones that contain both coding and 3' non-coding exons, only 3' non-coding sequences participate in the reassociation reaction, thus addressing the problem raised by Ko (1990) regarding the potential cross hybridization between coding exons from gene family members that are represented at different frequencies in the original cDNA population, without however, having to sacrifice the quality of the normalized library by leaving behind all relevant coding sequence information.

In the normalized cDNA catalogue, the origin (tissue source) of each clone will be readily known by single pass sequencing from the 3' end. This will be possible because each library component of this cDNA catalogue will have a distinctive sequence fingerprint. For each library a slightly different primer will be utilized for first strand cDNA synthesis. All primers will have in common the recognition sequence for a rare restriction site (Pac I), for directional cloning, and an oligo-dT track to prime cDNA synthesis off the polyadenylate tail of the mRNAs. However, the few nucleotides that lie between the 5' Pac I recognition sequence and the 3' oligo-dT track will be different for each primer, thus allowing immediate origin identification for any clone of the catalogue by straightforward single pass 3' end sequencing.

Subtractive hybridization

Subtractive hybridization of nucleic acids has proven to be a powerful method to isolate differentially expressed genes (Klar et al., 1992; Dear et al., 1988; Lee et al., 1991;

Duguid et al., 1988; Yancopoulos et al., 1990; Owens et al., 1991; Travis et al., 1987; Loros et al., 1989; Sykes & Weiser, 1992; Dear et al., 1991; Hara et al., 1991; Kho & Zarbl, 1991; Sive & St. John, 1988).

Subtractive hybridization experiments typically involved hybridizing first-strand cDNA (tracer) with an excess of poly (A)⁺ RNA (driver). The remaining single-stranded cDNAs were separated from the DNA-RNA hybrids by HAP chromatography and either cloned (Travis & Sutcliffe, 1988) or used as a probe in a differential screening procedure (Miller et al., 1987).

Simpler and more efficient methods for subtractive hybridization have now been described. Rubenstein et al. (1991) described a method according to which photobiotinylated single-stranded phagemids from a directionally cloned cDNA library were used as drivers in a hybridization with tracer amounts of complementary single-stranded phagemids. After binding to streptavidin and extracting with phenol:chloroform, the unhybridized single-stranded circles (subtracted library) were recovered from the aqueous phase, converted to partially duplex circular molecules (for improvement of electroporation efficiencies) and electroporated into bacteria. Swaroop et al. (1991) successfully isolated a number of retina-specific clones by a very simple procedure involving hybridization of in vitro synthesized biotinylated RNA (run-off transcription of a directionally cloned cDNA library in the presence of Bio-11-UTP) with single-stranded phagemids from a directionally cloned cDNA library. DNA-RNA hybrids were captured by affinity to vectrex-avidin (Vector Laboratories) and the single-stranded circles (subtracted library) were eluted, precipitated with glycogen and directly electroporated into bacteria.

The method used is very similar to that described by Swaroop et al. (1991). The novelty of this approach, however, is that normalized libraries, both as drivers and tracers, in all subtractive hybridization experiments will be utilized, a feature that should improve the overall efficiencies of subtraction.

This invention will be better understood from the Experimental Details which follow. However, one skilled in the art will readily appreciate that the specific methods and results discussed are merely illustrative of the invention as described more fully in the claims which follow thereafter.

Experimental Details

Construction of directionally cloned cDNA libraries in phagemid vectors

Existing protocols to construct directionally cloned cDNA libraries in phagemid vectors (Soares, 1993) have been optimized in an effort to minimize some of the most widely acknowledged problems with cDNA libraries (Adam et al., 1991), i.e., a) high frequency of clones with small size inserts; b) large number of clones with long polyadenylate tails; c) detectable (but undetermined) frequency of chimeric clones; and d) undesirable number of recombinant clones.

The general scheme for construction of directionally cloned cDNA libraries can be outlined as follows: a) a Not I-(dT) 18 oligonucleotide [or Pac I-(dT) 18] is utilized as primer for first strand cDNA synthesis with RNAse H⁻ Reverse Transcriptase from Moloney Murine Leukemia Virus (Gibco®-BRL); b) "one tube" first and second strand cDNA syntheses are performed essentially as described (D'Alessio et al., 1987); c) double-stranded cDNAs are polished with T4 DNA Polymerase, size selected on a Bio-Gel A-50 m column as described (Huynh et al., 1985) and ligated to a large excess of adaptor molecules (for the brain library described below which was constructed in the Lafmid BA vector applicants used Hind III adaptors, but for all libraries that applicants are planning to construct in the pT7T3-Pac I vector, applicants will utilize Eco RI adaptors instead); d) cDNAs are treated with T4 Polynucleotide Kinase to phosphorylate the adaptor ends (one of the two oligonucleotides of the adaptor molecule has a 5'OH to prevent concatemerization of adaptors), digested with Not I (or Pac I, depending on the primer utilized for 1st strand cDNA synthesis), size selected again over a BioGel A-50 m column and ligated directionally into the Not I and Hind III (Lafmid BA vector) or Pac I and Eco RI (pT7T3-Pac vector) sites of a phagemid vector; e) the ligation mixture is electroporated into bacteria and propagated under ampicillin selection; f) to eliminate complete from the library all clones that contain inserts shorter than 500 bp, the non-recombinants, and most existing chimeric clones, a plasmid preparation of the library is linearized with Not I (or Pac I), electrophoresed on an agarose gel and the linear recombinant molecules containing cDNAs larger than 500 bp are purified off the gel with β-agarose and recircularized in a large volume ligation reaction; and g) the ligation mixture is electroporated into bacteria and propagated under ampicillin selection to generate a cDNA library with an average size insert of 1.7 kb, no inserts shorter than 500 bp and a very low background of non-recombinant clones.

The following is a brief discussion of the modifications that were introduced to address each of the specific problems mentioned above.

Clones with small size inserts

This problem was solved by strictly size selecting the cDNAs over a 32 cm long-0.2 cm wide BioGel-A50 m column as described (Huynh et al., 1985). Although time consuming, this column is very reliable and reproducible. There are two rounds of size selection; one right after second strand synthesis (before adaptor ligation) and a second after adaptor ligation, just prior to setting up the ligation to the cloning vector. In addition, applicants have introduced a gel purification step after cloning and propagation in bacteria; supercoiled plasmid DNA from the library is linearized by Not I (or Pac I, depending on the primer utilized for first strand cDNA synthesis) digestion, and electrophoresed on a 1% agarose gel; and the DNA smear corresponding to cDNAs with insert sizes larger than 500 bp is cut off the gel, casted into a low melting point agarose gel, and electrophoresed backwards to sharpen the DNA smear. Library DNA is then purified by digestion of the gel slice with β-agarose. Following a ligation reaction performed under conditions that promote recircularization only, the DNA is electroporated into bacteria (DH10B, BRL®) and propagated under ampicillin selection. The exact reaction conditions to promote recircularization rather than inter-molecular ligations can be determined by the formula $3.3/\sqrt{\text{kb}} \, \mu g/ml$ as discussed by Smith et al. (1987).

The end product is a library with an average size insert of 1.7 kb (based on restriction digestion analysis of 900 clones (Adams et al., submitted), and no inserts shorter than 400 bp. Furthermore, non-recombinants (vector only) are practically undetectable [only two out of 1,500 randomly picked clones (Adams et al., submitted); or 1 out of 493 (Khan et al., 1992).

Long polyadenylate tails

This problem could be practically eliminated by increasing the amount of the Not I-(dT)-oligonucleotide utilized to prime first strand cDNA synthesis. The rationale behind this idea was that if the poly(A) tails of the mRNAs were completely saturated with primers, only the most proximal primer could be extended to reverse transcribe the mRNA [reverse transcriptase cannot strand displace efficiently (Kornberg & Baker, 1992)]. Extension of any other primer would be limited to its distance to the next downstream primer, thus generating very small fragments that could be easily eliminated by an efficient size selection procedure.

The efficiency of this modification to shorten the length of the poly(A) track present at the 3' end of all clones has been firmly documented by sequencing analysis of over 2,000 randomly picked clones from an infant brain library (Khan et al., 1991; Adams et al., submitted).

Chimeric cDNA clones

Chimeric clones often result from blunt end ligation of cDNA molecules during the reaction in which adaptors are ligated to the cDNAs. To prevent formation of these cloning artifacts, adaptor molecules must be present in vast excess over cDNAs in this ligation reaction. Such conditions can be easily satisfied only if the cDNAs are efficiently size selected prior to ligation. This is so because a large amount of very small fragments of double-stranded tail are generated during cDNA synthesis. In terms of pmoles of ends these short cDNAs constitute a very significant fraction of the cDNA molecules and they can take up most of the adaptor molecules. Therefore, it is important that the cDNAs are efficiently size selected after second strand synthesis before ligation to the adaptors. As mentioned above, chromatography over a Bio-Gel A-50 m column is a very reliable method for size selection of cDNAs.

Another step where chimeric clones can be generated is during ligation of the cDNAs to the cloning vector. This is less likely to occur, however, because the cDNA have two different ends and three cDNA molecules must be joined together before they can be ligated to a vector molecule. Nonetheless, in order to minimize the probability of formation of chimeric clones during this ligation reaction, vector should be present in excess over cDNAs. Since dephosphorylation usually reduces cloning efficiencies, the approach of not dephosphorylating the vector and using it in only a slight excess is favored; a twofold excess over cDNAs seems to be a good compromise. Under these conditions, chimeric clones are unlikely to be formed and the background of non-recombinant clones still remains low.

An important feature of these directionally cloned cDNA libraries is that a major fraction of existing chimeric clones can be easily detected. A bona fide cDNA clone from this library should be linearized with Not I (or Pac I, depending on the primer utilized for first strand cDNA synthesis). Release of a fragment after digestion is indicative of chimerism. It should be acknowledged, however, that even if digestion indicates the presence of a single Not I (or Pac I) site, the possibility remains that the clone is chimeric and one of the sites was destroyed upon cloning.

It should be emphasized that a significant percent of chimeric clones are eliminated at the final size selection step in which the library (as plasmid DNA), is linearized with Not I (or Pac I) and the recombinant molecules containing cDNA inserts larger than 500 bp are gel purified, recircularized and electroporated into bacteria.

Non-Specific priming events

Some precautions are necessary to avoid non-specific priming at GC-rich regions of the mRNAs when using large amounts of the Not I-(dT)18 primer for first strand cDNA synthesis. Most importantly, the reaction mixture should be pre-incubated at 37° C. before the addition of reverse transcriptase. It was observed that if the enzyme is added to the reaction mixture while it is at room temperature, an appreciable number of clones without tail can be obtained. For example, clones for the mitochondrial 16S rRNA which resulted from priming events at two sites of the RNA sequence that differ from the recognition sequence of the Not I restriction enzyme by a single nucleotide have been obtained. Presumably, if a GC-rich cluster is flanked by a few (A)s located upstream on the RNA, the Not I sequence (GCGGCCGC, SEQ ID No. 1) of the primer can anneal to it while most of the oligo-dT tail loops out. The end product of such non-specific priming events can be a clone without a tail or a clone with a very short tail (shorter than the primer). These clones are easily detected because a bona fide polyadenylation signal sequence (AAUAAA, SEQ ID No. 2) cannot be identified at the appropriate position.

It is to avoid such non-specific priming events that applicants are planning to replace the Not I-(dT) 18 oligonucleotide originally utilized to prime first strand cDNA synthesis in applicants' protocol, with a (GC-less) Pac I-(dT)18 primer.

Modifications

The plan is to modify the protocol to replace Not I by Pac I. In this regard, a Pac I-(dT)18 oligonucleotide has been synthesized to be utilized as primer for first strand cDNA synthesis and a library is currently under construction. Control digestions have been performed to show that the recognition sequence for the enzyme Pac I occurs very rarely on cDNAs. In positive control digestions, Pac I cut a supercoiled plasmid containing a single Pac I site with no difficulty; prolonged incubations of the enzyme with a different supercoiled plasmid that did not have a Pac I site, did not result in detectable conversion of supercoiled to relaxed circles. Altogether, these results indicated that Pac I (NEB) is a very good enzyme.

Because the Lafmid BA vector, which was utilized for construction of the infant brain cDNA library described below, does not have the promoters for in vitro synthesis of RNA, applicants decided to switch to another cloning vector (pT7T3, Pharmacia®). There was no reason to modify the Lafmid BA vector to include RNA promoters since other phagemids are already available that have all features that was needed. Accordingly, the polylinker of the pT7T3 phagemid vector (Pharmacia®) was modified to include a Pac I site. This modified vector was named pT7T3-Pac by applicants. This vector has all the features that was needed to normalize and subtract libraries, i.e., it has an fl origin for production of single-stranded circles upon super-infection with a helper phage and it contains both the T3 and T7 promoters for in vitro synthesis of RNA.

The sequence of the polylinker of the pT7T3-Pac vector is:

```
         Sfi I      Eco RI      SnaBI       BamHI      Pac I
5'GGCCCTCGAGGCCAAGAATTCCCGACTACGTAGTCGGGGATCCGTCTTAATTA

Not I    HindIII
   AGCGGCCGCAAGCTT 3'   (SEQ ID No. 3).
```

The plan is to clone cDNAs directionally into the Eco RI and Pac I sites of this phagemid vector. Accordingly, Pac I will be utilized to linearize the library for the gel purification step. Since (mRNA-like) and antisense RNA can be transcribed in vitro off the existing T7 and T3 promoters, respectively, which immediately flank the polylinker. Single-stranded circles will have the mRNA-like strand. Therefore, run-off transcripts from the T3 promoter will be complementary to the library in the form of single-stranded circles.

Preparation of high efficiency electrocompetent bacteria and propagation of CDNA libraries Protocols to make electrocompetent bacteria which yield cells with electroporation efficiencies of $6 \times 10^{10}$ cfu/μg CsCl-banded supercoiled plasmid DNA have been optimized. A side by side comparison of the electroporation efficiencies of the electrocompetent bacteria used with that of the commercially available Electromax (BRL®) have been done. The BRL cells had the advertised efficiency of $10^{10}$ cfu/μg whereas applicants' had a 6 fold higher efficiency. Very high efficiency electrocompetent bacteria was needed for some of the work done in the laboratory. That was the reason why some time was invested on the improvement of this protocol. According to the existing protocols (Dower et al., 1988; Zabarovsky & Winbert) the bacterial culture is grown to an $A_{600}$=0.5 to 1, when the cells are than harvested and sequentially washed with large volumes of 10% or 20% glycerol. The highest electroporation efficiencies were achieved when the cultures were harvested at a lower OD ($A_{600}$=0.2): the % live cells at the end of all manipulations was higher, and electroporation efficiencies of $6 \times 10^{10}$ cfu/μg were reproducibly obtained for DH10B bacteria. Applicants have two types of electrocompetent bacteria: DH10B and dH5αF'.

As a rule of thumb, the only time when a cDNA library is propagated into male (F') bacteria (dH5αF') is for production of single-stranded circles. For all other purposes (especially for amplification) female bacteria (DH10B) was used because they cannot get infected by filamentous phage. Despite all precautions that are taken to avoid "undesirable contaminants", helper phage can accidentally get introduced into a culture. It was observed that if a library is superinfected with helper phage for a prolonged time, differential growth of clones becomes apparent. That is why for single-stranded production, the culture was only allowed to be in the presence of helper phage for a limited amount of time. Thus, to avoid taking any chances, DH10B cells were used for most applications.

Propagation of cDNA libraries in the form of single-stranded circles

1–10 ng supercoiled plasmid DNA representing the entire library is electroporated into dH5αF' grown at 37° C. for one hour and then propagated under ampicillin selection to mid-log phase. The culture is then diluted 100 fold with fresh medium and grown in the presence of 0.2% glucose under ampicillin selection to $A_{600}$=0.2. At this time, the culture is superinfected with a 10–20 fold excess of helper phage (R408 or M13KO7) and grown for only four hours. The culture must be harvested at that time. Prolonged growth in the presence of helper phage is detrimental and must be avoided. The yield of single-stranded material will not be any better while differential growth will start to become apparent. To be safe, applicants routinely verified that no helper phage got accidentally introduced into the starting culture as follows: a sample of the culture is span down, and a drop of the supernatant is spotted onto a lawn of infectable bacteria to show that it can yield no plaques.

Single-stranded DNA is prepared according to standard protocols which involve precipitation of packaged single-stranded circles with polyethyleneglycol and phenol/Sevag extractions.

Applicants have performed control colony hybridization experiments to show that the frequency of several of the abundant clones (α-tubulin, elongation factor 1α, β-tubulin and myelin basic protein) was absolutely identical in both the starting double-stranded library and in the library in the form of single-stranded circles. Thus, if prepared under the conditions described above, the library in the form of single-stranded circles is perfectly representative of the starting library.

cDNA library normalization

Applicants have developed (Soares & Efstratiadis, manuscript in preparation; see FIG. 1) a method for normalization of directionally cloned cDNA libraries constructed in phagemid vectors and successfully utilized it to normalize an infant brain cDNA library (see Table I).

Applicants' method differs from other existing procedure (Ko, 1990; Patanjali et al., 1991) in several aspects. First, instead of utilizing PCR-amplified cDNA fragments as the starting material for the kinetic approach, library DNA was utilized in the form of partially duplex circles. (It should be emphasized that the double-stranded region of these circles correspond primarily to the 3' non-coding sequences. These partially duplex molecules are then melted and reassociated, and the remaining (non-reassociated, normalized) single-stranded circles are HAP-purified and electroporated into bacteria. Thus, the reassociation reaction involves primarily 3' untranslated sequences. It should also be noted that in our method, the single-stranded (normalized) material at the end of the melting/reassociation reaction consists of already cloned cDNAs, as opposed to relatively short single-stranded cDNA molecules that need to be amplified by PCR and cloned in order to generate a normalized library (Ko, 1990; Patanjali et al., 1991).

The cDNA clones in the normalized infant brain cDNA library generated by this protocol contain large size inserts (average of 1.7 kb). Non-recombinant (vector only) molecules have not yet been detected in the normalized library (they were already almost undetectable in the library before normalization and they should have been left behind in the procedure because they could not have gotten primed in the first place). Digestion of over 200 clones with Not I failed to detect a single-chimeric clone (as discussed, non-chimeric clones should only be linearized with Not I; release of a Not I fragment would be indicative of chimerism).

For the construction of the infant brain (non-normalized) library, a Not I-(dT)18 oligonucleotide [5'AACTGGAA-GAATTCGCGGCCGCAGGAA(T)18, SEQ ID No. 4] was utilized as primer for first strand cDNA synthesis. After ligation to Hind III adaptors, the cDNAs were digested with Not I (after appropriate size selections) and directionally cloned into the Hind III and Not I sites of a plasmid vector (lafmid BA) derived from pEMBL. The polylinker of the lafmid BA vector contains the following restriction sites: 5' Hind III; Bam HI; Not I; and Eco RI 3'.

Single-stranded library DNA represents the message (mRNA-like) strand and therefore all single-stranded circles contain a short polyadenylate tail at their 3' end (except for the non-specific priming events discussed before, where priming took place at GC-rich regions rather than at the polyadenylate tail of the mRNAs).

Figure 1:
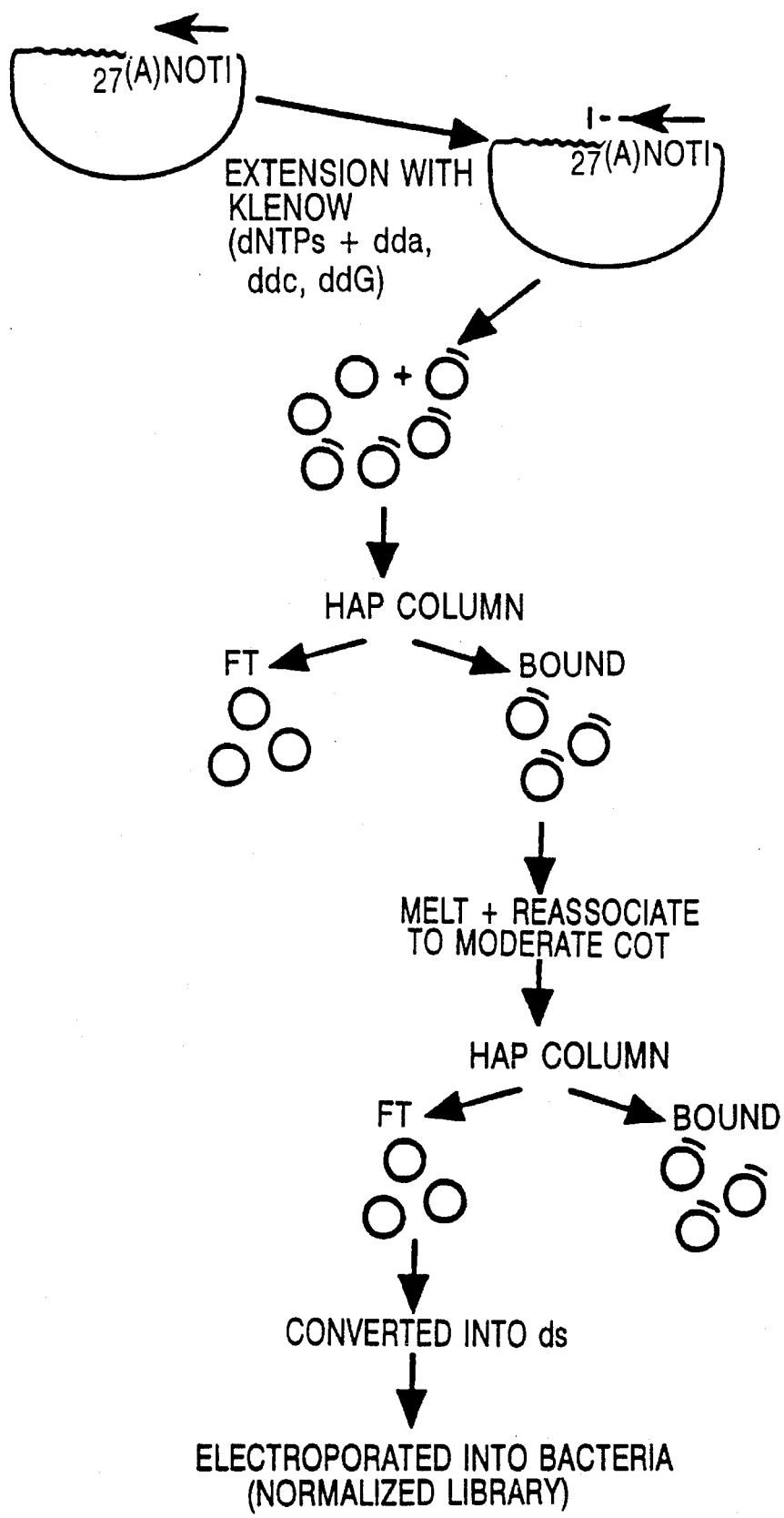
FIG. 1 Schematic Representation of the Normalization Protocol.

Following is a brief description of the steps involved in the normalization of this infant brain cDNA library (See FIG. 1 for a schematic representation).

a) Single-stranded library DNA was purified from any residual double-stranded plasmid contaminant by HAP column chromatography under standard aqueous conditions (Britten et al., 1974), in a jacketed column at 60° C. It should be noted that single-stranded circles are very sensitive to high temperatures (electroporation efficiencies of single-stranded circles drop very dramatically upon boiling, for example). However, a quick purification through a 60° C.-HAP column does not damage single-stranded circles in applicants' hands. HAP-purified single-stranded DNA was then purified from any residual amount of tRNA and from most of the helper phage DNA by agarose gel electrophoresis.

The gel slice containing the single-stranded library DNA smear was casted into low melting point agarose. The current was reversed and the low melt agarose gel was run for a short time just to sharpen the smear. DNA was isolated after digestion with β-agarose (NEB). This gel purification step proved to be necessary to avoid undesirable internal priming events promoted by small RNA oligonucleotides (breakdown products from RNAse A digestion of tRNAs). The single-stranded DNA was never exposed to UV light (a small fraction of it was run on a separate lane, which was exposed to UV and served as a reference; this DNA was not used).

b) 0.6 pmoles of a ½ Not I-(dT)15 oligonucleotide [5' GGCCGCAGGAA(T)15, SEQ ID Nos. 5 and 6] were added to 0.3 pmoles of single-stranded circles (library DNA) in a 10 μl reaction containing 30 mM Tris pH7.5-50 mM NaCl-15 mM $MgCl_2$-1 mM DTT-0.1 mM each deoxynucleotide (dA, dC, dT, and dG)-2.5 mM each dideoxynucleotide (ddA, ddC and ddG; but no ddT) and a trace of $\alpha^{32}$PdCTP. The mixture was first incubated for five minutes at 60° C., and then for fifteen minutes at 50° C. (annealing temperature). The temperature was lowered down to 37° C., 5 units of Klenow enzyme were added and the reaction remained at 37° for thirty minutes. Fifteen such reactions were carried out in parallel.

The size distribution of the synthesized strand was rather narrow (160t±20 nt; see FIG. 2, lane 4). Klenow was the only polymerase among the several that were tried that yielded such a sharp size distribution. Since 3' non-coding exons are usually larger than 300 nt (average of 600 nt), the vast majority of the synthesized material should correspond to 3' untranslated sequences.

In the next step these partially duplex circular molecules were purified from any remaining (unprimed, unextended) single-stranded circles by HAP chromatography (applicants have actually also tried incorporating biotinylated nucleotides during the extension reaction to allow capturing of the partial duplex circles by affinity to streptavidin-coated solid supports; the results were not satisfactory in applicants' hands especially because the procedure resulted in a dramatic impairment of electroporation efficiencies).

c) All 15 reactions were pooled together and stopped with EDTA (20 mM f.c.). The sample was extracted with phenol+Sevag, and phosphate buffer (PB) was added to a final concentration of 0.12M. 2 mls of 60° C.-prewarmed 0.12M PB-10 mM EDTA-1% SDS containing 50 μg denatured sonicated solmon sperm DNA were added to the sample and the mixture was passed through a HAP column at 60° C. The column (0.4 g HAP, about 1 ml bed colume) had been pre-equilibrated with 0.12M PB-10 mM EDTA-1% SDS. After a wash with 6 mls of 0.12M PB-10 mM EDTA-1% SDS, the partial duplex circles (HAP-bound) were eluted off the column with 6 mls of 0.4M PB-10 mM EDTA-1% SDS. 14 mls $H_2O$ containing 50 μg denatured sonicated salmon sperm DNA were added to this eluate to lower the PB concentration down to 0.12M, the column was reequilibrated with 0.12M PB-10 mM EDTA-1% SDS and the sample was passed through the column again.

This second passage through HAP was necessary to eliminate the background of single-stranded circles that bind non-specifically to HAP; every time single-stranded DNA is passed through HAP, about 0.1% of it binds non-specifically. However, by passing it through twice, this background becomes negligible (0.1×0.1= 0.01%). The column was washed with 6 mls 0.12M PB-10 mM EDTA-1% SDS and the partially duplex circles (HAP-bound) were eluted with 6 mls 0.4M PB-10 mM EDTA-1% SDS.

d) The eluate was desalted over a Nensorb column (DuPont). DNA was eluted off the Nensorb column with 1 ml 20% n-propanol in $H_2O$, vacuum-dried for 30 minutes, (at this point, an aliquot of the material was applied on a 6% sequencing gel for determination of the sizes of the extended material; see FIG. 2) and ethanol precipitated.

e) The DNA pellet was resuspended in 2.5 μl formamide and heated for 3 minutes at 80° C. under a drop of mineral oil. 1 μl 5 μg/μl oligo-(dT)25–30, 0.5 μl 1 μg/μl½Not-(dT)15 oligonucleotide, 0.5 μl 5M NaCl, and 0.5 μl 0.1M Tris-0.1M EDTA (total 5 μl) were added and the mixture was incubated at 42° C. [oligo-(dT)25–30 and ½Not-(dT)15 oligonucleotides were present to block the polyadenylate tails]. Small aliquots were taken at various times. The best normalization results (see Table 1) were obtained after 13 hours of incubation.

f) In this next step, the remaining (normalized) single-stranded circles were separated from the (reassociated) partially double-stranded circular molecules by HAP chromatography.

To 0.5 μl of the hybridization mixture, 5 μg were added of denatured sonicated salmon sperm DNA+2 mls of 60° C. prewarmed 0.12M PB-10 mM EDTA-1% SDS and the sample was passed through 0.4 g HAP. The column was washed with 6 mls 0.12M PB-10 mM EDTA-1% SDS and the HAP-flow-through (containing the normalized single-stranded circles) was passed through a second (fresh) HAP column just to minimize the chance that any residual amount of partially double-stranded molecules escaped from binding through some undetected small channel in the column; by passing it through a fresh column this potential problem was eliminated. The column was washed with 6 mls 0.12M PB-10 mM EDTA-1% SDS and the flow-through material (normalized single-stranded circles) was desalted through a Nensorb column as described above. HAP-bound DNA from the first column was also purified.

g) At this point, one can either directly electroporate the single-stranded circles (HAP-flow-through) into competent DH10B bacteria, or one may convert them into partially double-stranded circles (by primed extension) in order to improve their electroporation efficiencies by 50–100 fold. Such extensions can be primed with random hexamers, the M13 Universal primer, or an oligonucleotide complementary to a region of the ampicillin resistance gene. Applicants have successfully utilized all three of them.

After 1 hour at 37° C., an aliquot of the culture (10 μl out of 100 mls) was plated on an LB agar plate containing ampicillin for determination of total number of transformants, ampicillin was added to the culture to a final concentration of 75 μg/ml, and the bacteria were propagated until the culture reached mid-log phase. Supercoiled plasmid DNA (normalized library) was extracted by alkaline lysis and purified over a Qiagen mid-size column. 2.5 million transformants were obtained from the 0.5 μl of hybridization mixture that were processed.

Characterization of the normalized infant brain library by colony hybridization with a panel of probes Applicants have performed colony hybridization experiments to assess the frequency of a number of cDNA probes in the infant brain library both before and after normalization (see Table 1). The results indicated that the normalization was successful. The frequency fold variation observed for 13 cDNA probes that were tested in the starting library was of 575 (cDNA probe elongation factor 1α=4.6%; cDNA probe Cot250#1-unknown=0.008%). In contrast, the frequency variation of 23 cDNA probes that were tested in the normalized library was only of 30 fold (cDNA probe γ-actin=0.1%; cDNA probe MAP=0.0033%). Eight of these cDNA probes corresponded to cDNA clones that were randomly picked up from the normalized library (they were all given the prefix "normalized" in Table I, column 1): their frequencies were within a 17 fold range (the most frequent was at 0.05% and the least frequent at 0.003%).

It should be mentioned that the number of positive hybridizers observed in both libraries (before and after normalization) with a human Cot1 DNA probe was within a twofold range. Similar results were also obtained by Ko (1990) and Patanjali et al. (1991). When divergent members of repetitive DNA families reassociate, they form imperfect hybrids that are likely not to bind to hydroxyapatite under standard conditions. Under applicants' conditions only double-stranded DNA 100 bp or longer (without any mismatched bases) can bind to HAP. This is a very desirable feature of the HAP which assures us that even those rare cDNA clones that happen to contain a repetitive DNA element within their 3' noncoding sequences will be represented in the normalized library.

Overall design and methods

The plan is to construct cDNA libraries from a number of different tissues, to normalize each one of them separately, to pool all the individual normalized libraries and re-normalize them together to generate a human cDNA catalogue. Each individual library will have a distinctive sequence identifier, so that information on the origin of any clone of the cDNA catalogue can be immediately retrieved.

These resources will provide a unique opportunity for the performance of a series of subtractive hybridizations involving normalized libraries. Furthermore, these sequence identifiers will allow immediate verification of tissue-specificity of clones from a subtracted library by straightforward single pass sequencing.

Construction an normalization of cDNA libraries

Human tissues are obtained for construction of the following cDNA libraries:

Infant brain library

Infant brain (total brain from a 3-month old human infant who died in consequence of spinal muscular atrophy). High quality mRNA is available. This mRNA was already utilized for construction of a cDNA library in the lafmid BA vector. However, because the lafmid BA vector does not allow for in vitro synthesis of RNA, a feature that is required in applicants' strategy for library subtraction, applicants will utilize this mRNA again to construct a cDNA library in the pT7T3-Pac vector.

Adult brain library

Adult brain (a collection of tissue samples representing all regions of the brain with the exception of hippocampus). Power was prepared from multiple areas of the brain and pooled. These areas included frontal, parietal, temporal and occipital cortex from the left and right hemispheres, subcortical white matter, basal ganglia, thalamus, cerebellum, midbrain, pons and medulla. High quality RNA is already available.

Adult hippocampus library

Adult hippocampus (obtained from the same brain of that utilized for construction of library #1). Both hippocampi were utilized. High quality RNA is already available.

Other libraries from different human tissue such as fetal brain, fetal liver, infant liver female, infant spleen, infant heart, infant lung, infant muscle, adult spinal cord, placenta, and fetal eyes.

Additional libraries may be constructed depending on availability of good tissue sources. As mentioned above, each of these cDNA libraries will have a characteristic sequence identifier, which will be provided by the oligonucleotide utilized to primer first strand cDNA synthesis. The following is a list of these primer sequences: 5' TTT TTT TTAATTAA TTTT TT TTT TTT TTT TTT 3' (SEQ ID No. 8); 5' TTT TTT TTAATTAA GAGT TT TTT TTT TTT TTT TTT 3' (SEQ ID No. 9); 5' TTT TTT TTAATTAA TAGG TT TTT TTT TTT TTT TTT 3' (SEQ ID No. 10); 5' TTT TTT TTAATTAA CGTC TT TTT TTT TTT TTT TTT 3' (SEQ ID No. 11); 5' TTT TTT TTAATTAA TGCT TT TTT TTT TTT TTT TTT 3' (SEQ ID No. 12); 5' TTT TTT TTAATTAA AGCA TT TTT TTT TTT TTT TTT 3' (SEQ ID No. 13); 5' TTT TTT TTAATTAA GCTA TT TTT TTT TTT TTT TTT 3' (SEQ ID No. 14); 5' TTT TTT TTAATTAA CAAT TT TTT TTT TTT TTT TTT 3' (SEQ ID No. 15); 5' TTT TTT TTAATTAA CTGA TT TTT TTT TTT TTT TTT 3' (SEQ ID NO. 16); 5' TTT TTT TTAATTAA AAAG TT TTT TTT TTT TTT TTT 3' (SEQ ID No. 17); 5' TTT TTT TTAATTAA ACTG TT TTT TTT TTT TTT TTT 3' (SEQ ID No. 18); 5' TTT TTT TTAATTAA ATCC TT TTT TTT TTT TTT TTT 3' (SEQ ID No. 19); 5' TTT TTT TTAATTAA CCAC TT TTT TTT TTT TTT TTT 3' (SEQ ID No. 20); and 5' TTT TTT TTAATTAA GGAA TT TTT TTT TTT TTT 3' (SEQ ID No. 21)

All primers will have the recognition sequence for the Pac I restriction endonuclease (TTAATTAA, SEQ ID No. 7), for directional cloning of cDNAs. The library sequence identifiers are underlined.

It is not the intention of this invention to be limited by the above embodiments.

This approach is to introduce a sequence ID which can be of any number of nucleotides and can be of any sequence. Such IDs should be present in the primer which is used to prime the first strand cDNA between the recognition sequence for a rare cutter and an oligodT stretch. The use of Pac I as a rare cutter sequence is simply an example. An ordinary skilled artisan will be able to use this approach with other rare cutter sequence after reading this specification.

All cDNA libraries may be constructed in the pT7T3-Pac I vector. Applicants will follow the above-described protocols to construct all libraries. The only modification will be that instead of utilizing the Not I-d(T) 18 oligonucleotide to prime first strand cDNA synthesis, applicants will use the Pac I-d(T)18 oligonucleotides described above. Accordingly, the double-stranded cDNAs (after ligation to Eco RI adapters and required purifications) will be digested with Pac I (as opposed to Not I) and directionally cloned into the Pac I and Eco RI sites of the pT7T3-PacI vector. As discussed above, applicants decided to switch from Not I (GCGGCCTC, SEQ ID No. 22) to Pac I (TTAATTAA, SEQ ID No. 23), to avoid some of the non-specific priming events that can occur at GC-rich regions of mRNAs when priming first strand cDNA synthesis with the Not I-(dT)18 oligonucleotide.

Each individual cDNA library will be propagated in the form of single-stranded circles (mRNA-like strand), and normalized separately, according to the established protocol described in the Preliminary Results section. The only necessary modification regards the oligonucleotide to be utilized in the controlled primed extension reactions of the normalization procedure (see FIG. 1). Applicants will synthesize a degenerate oligonucleotide [5'CCGCTTAAT-TAANNNN(dT15, SEQ ID No. 24) named ½Not-Pac-(dT)15'] specific for this purpose. Its 5' most nucleotides (CCGC, SEQ ID No. 25) will be complementary to the sequence of the vector that immediately flanks the Pac I cloning site, thus serving as an anchor point which will allow applicants to raise the stringency of the annealing reaction and therefore minimize non-specific priming events. The same rationale was followed for the choice of the ½Not-(dT) primer utilized in the extensions for the successful normalization of the infant brain library.

If for any reason this primer will not work satisfactorily, applicants have the choice of priming each single-stranded individual library with its respective (and specific) Pac-(dT) 17–18 oligonucleotide.

Assessment of normalization will be done for each individual library by colony hybridization screenings with a panel of cDNA probes representing the three frequency classes of mRNAs, similarly to what was done to characterize the normalized infant brain library (see Table 1).

TABLE 1

FREQUENCIES OF cDNA CLONES IN AN INFANT BRAIN LIBRARY BEFORE AND AFTER NORMALIZATION

| cDNA clone | Frequencies | |
| --- | --- | --- |
| | Before Normalization | After Normalization |
| Elongation factor 1α | 4.6% | 0.04% |
| α Tubulin | 3.7–4.4% | 0.045% |
| Myelin basic protein | 1% | 0.09% |
| γ-actin | 0.35% | 0.1% |
| Aldolase | 0.6% | 0.03% |
| Hsp 89 | 0.4% | 0.05% |
| Secretogranin | 0.07–0.1% | 0.01% |
| Cot109+103-bio20-unknown | 0.08% | 0.005% |
| CH13-cDNA#20-endogenous retrov | 0.02% | 0.02% |
| Cot109+103#4-unknown | 0.014% | 0.005% |
| Histone H2b.1 | 0.014% | 0.015% |
| CH13-cDNA#8-unknown | 0.01% | 0.035% |
| MAP | Not determined | 0.0033% |
| Cot250#1-unknown | 0.008% | 0.015% |
| YAC4 cDNA#1-unknown | Not determined | 0.006% |
| Normalized-cDNA #103-unknown | Not determined | 0.013% |
| Normalized-cDNA | Not determined | 0.003% |

TABLE 1-continued

FREQUENCIES OF cDNA CLONES IN AN INFANT BRAIN LIBRARY BEFORE AND AFTER NORMALIZATION

| cDNA clone | Frequencies | |
| --- | --- | --- |
| | Before Normalization | After Normalization |
| #120-unknown | | |
| Normalized-cDNA #122-unknown | Not determined | 0.007% |
| Normalized-cDNA #138-unknown | Not determined | 0.02% |
| Normalized-cDNA #141-unknown | Not determined | 0.05% |
| Normalized-cDNA #142-unknown | Not determined | 0.01% |
| Normalized-cDNA #143-unknown | Not determined | 0.04% |
| Normalized-cDNA #114-unknown | Not determined | 0.007% |

Construction of the human cDNA catalogue

1–10 ng of supercoiled plasmid DNA from each of the 14 normalized libraries will be separately electroporated into dH5αF' and each culture (200 mls) will be grown under ampicillin selection to early-log phase ($A_{600}$=0.1 –6×10$^7$ colonies per ml culture). 10$^7$ cells from each of the 14 cultures will then be pooled together (14×10$^7$ or 1.4×10$^6$ total cells), and diluted 50-fold with fresh broth containing 0.2% glucose and 75 µg/ml ampicillin. This culture will be grown to an $A_{600}$=0.2, when it will then be superinfected with a 10–20 fold excess of helper phage M13K07. After exactly 4 hours the culture will be harvested, single-stranded DNA will be isolated and purified through HAP and agarose gel electrophoresis as described in the Preliminary Results section. This material will then undergo the normalization protocol to generate the human cDNA catalogue. Applicants will utilize the ½Not-Pac-(dT) 15 degenerate oligonucleotide for the controlled primed extension reaction involved in the normalization procedure. If this primer will prove inadequate, applicants have the choice of performing the annealing reaction in the presence of all 14 specific Pac-(dT) 17–18 oligonucleotides.

As in the other cases, the extent of normalization of the cDNA catalogue may be assessed by screening the library (colony hybridization) with a panel of cDNA probes representing prevalent, moderate and rare mRNAs.

In addition, 100 randomly picked clones (single pass sequencing from the 3' end only) will be sequenced to estimate the frequency of each library component in the cDNA catalogue.

Subtractive hybridization of normalized libraries

The Strategy to be utilized for subtractive hybridization of cDNA libraries will be very similar to that described by Swaroop et al. (1991) for the isolation of retina specific cDNAs. Two strategies will be compared.

(1) Synthesize biotinylated run-off transcripts with Bio-11-UTP (Enzo Biochem) and then use vectrex-avidin (Vector Laboratories) to capture the hybrids and thereby purify (flow-through) the unhybridized single-stranded circles (tissue-specific sublibrary) which can then be electroporated into bacteria (after conversion to partial duplexes by random priming for improvement of electroporation efficiencies).

(2) Synthesize non biotinylated run-off transcripts and then use HAP column chromatography to separate the remaining single-stranded material (subtracted library, HAP-flow-through) from the RNA-DNA hybrids (HAP-bound).

Supercoiled plasmid DNA from a normalized library will be linearized with Sfi I and in vitro transcribed from the T3 promoter (run-off transcription) to generate large quantities of antisense RNA which will be complementary to any of the directionally cloned normalized libraries in the form of single-stranded circles (mRNA-like strand). The reactions will be performed with the "Riboprobe Gemini II In Vitro Transcription System" (Promega, Cat#P2570), according to the manufacturer's instructions. A cDNA in the pT7T3-Pac vector has been subcloned to test its ability to drive transcription off the T7 and T3 promoters, and very good yields of RNA were obtained in both cases. Very good yields of single-stranded DNA circles with this plasmid (better with M13K07 than with R408) are routinely obtained.

The in vitro synthesized RNA will then be hybridized to single-stranded circles from normalized libraries. However, since the first 15–20 nucleotides at the 5' end of the in vitro synthesized RNA will be complementary to the sequence of the polylinker immediately flanking the Pac I cloning site, precautions need to be taken to prevent hybridization between RNA and single-stranded circles through such sequences. Applicants plan to synthesize a "blocking" oligonucleotide, which will have the same sequence of the single-stranded circles in that region [5'(A)$_{18}$NNNNTTAATTAAGCGGCCGCAAGCTTATT 3', SEQ ID No. 26]. Thus, to prevent hybridization through such sequences the RNA will first be annealed to an excess of the blocking oligonucleotide, and then digested with RNAse H, which will eliminate that very sequence form the RNA (RNAse H attacks the RNA strand of a DNA:RNA hybrid). The sample will be digested with RNAse-free DNAse, which will destroy both the excess blocking oligonucleotide and the linearized plasmid DNA template, and then hybridized to the single-stranded circles.

Typically 0.2 μg of a single-stranded DNA will be hybridized to 20 μg of RNA for 72 hours at 42°–45° C. in a 10 μl reaction containing 0.5M Sodium Phosphate pH 7.2, 10 mM EDTA, 0.1% SDS, 50% formamide (Cot of approximately 3,000). The remaining single-stranded circles (normalized tissue-specific sublibrary) will be purified either by HAP chromatography or by affinity (lack of) to vectrex-avidin, as discussed above. Applicants have vast experience with HAP and applicants know for fact that it is very reliable for this kind of purification. Thus, at least this approach is guarantee to work, but nonetheless applicants will compare efficiencies with the alternate method. After purification, the single-stranded material will be converted to partially duplex DNA by random priming (just as applicants have been routinely doing at the end of the normalization procedure) and electroporated into bacteria for propagation under ampicillin selection.

Model system for optimization of conditions for subtractive hybridization of normalized libraries.

As a model system for optimization of conditions for subtractive hybridizations involving normalized libraries applicants will isolate hippocampus-specific cDNAs (see FIG. 3). Two normalized libraries will be utilized: adult brain library: a collection of tissue samples representing all regions of the brain with the exception of hippocampus) and adult hippocampus library, obtained from the same brain of that utilized for construction of the adult brain library). In vitro synthesized RNA from the adult brain library (driver) will be hybridized (high Cot) to a mixture of single-stranded circles from both adult brain and adult hippocampus libraries (tracers), and the remaining single-stranded circles (hippocampus-specific normalized sub-library) will be purified as discussed above. The presence in the hybridization of single-stranded circles from adult brain library will serve as a built in control. If completion of hybridization is achieved, no single-stranded circles from adult brain library should remain unhybridized. Verification that the subtracted library really corresponds to hippocampus-specific cDNAs will be straightforward by single-pass sequencing (3' end sequencing with the M13 Universal Primer or with a primer complementary to the T3 promoter) of a number of randomly picked clones from the subtracted library. This will be possible because clones from these two libraries can be discriminated by their specific sequence identifiers. So, if all clones from the subtracted library will indeed have the sequence identifier of the hippocampus library applicants will know that the subtraction worked efficiently and that applicants will have isolated a collection of hippocampus-specific cDNA clones.

It should be emphasized that the bound material (either HAP-bound or avidin-bound) will also be informative. Clones from the hippocampus library present in the bound fraction will represent mRNAs that are common to hippocampus and some other (or all other) region of the brain. However, applicants will concentrate on the flow-through (tissue-specific) material.

Since this will be a test system, applicants will (in addition to sequencing) also demonstrate tissue-specificity by RNAse protection assays (just this first time). Once verified, applicants will have established a very effective and straightforward way to isolate and verify tissue-specificity of a subtracted library. From there on applicants will do all verifications by single-pass sequencing only.

Applicants will certainly also sequence about 50 clones from the original mixture of single-stranded circles from adult brain and adult hippocampus libraries (the very mixture that will be used as tracer in the hybridization) to assess relative frequencies of clones from the two libraries (the expectation would be to find each at a frequency of about 50%). Applicants will then first sequence 20 clones from the subtracted library. Depending on the extent to which the ratio of clones from the two libraries deviated from the starting frequency of 50% each, applicants will decide whether or not a second round of hybridization should be performed. If it will be necessary applicants will just make single-stranded circles from the first subtracted sub-library and hybridize it to a large excess (100-fold) of in vitro synthesized RNA from library #1 again. Once the sequence data will indicate purity of the subtracted sublibrary (all hippocampus-specific clones) applicants will go on and sequence up to 100 clones to derive a solid and statistically significant number. Each clone will then be sequenced from both 5' and 3' ends. It is our experience that because the sequence obtained from 5' end of a clone will often correspond to coding information, the chances of identifying homologies through database searches increase rather significantly.

All DNA sequencing will be done using our ABI DNA Sequencer. Applicants also have a Biomek workstation where all sequencing reactions are routinely performed. Blast searches (Altschul et al., 1990) will be done through e-mail to the NCBI server. Applicants do database searches on a daily basis in the context of another ongoing project in the laboratory to isolate chromosome 13-specific cDNAs.

Finally, applicants will estimate the complexity of the subtracted library by performing a number of colony hybridization experiments. Since the subtracted library will be normalized, the frequency of any clone should be within a narrow range. Therefore, applicants should be able to estimate the total number of different clones in the subtracted library by hybridizing 10,000 or so colonies from the subtracted library with a battery of randomly picked cDNA probes from the same subtracted library. If for instance each of 10–20 probes will be represented at a frequency of 0.1–0.5% applicants will know that there might be 500–1,000 different hippocampus-specific cDNA clones in the subtracted library.

Subtractive hybridizations involving different normalized libraries and the cDNA catalogue.

Once applicants have optimized all conditions with the model system described above, applicants will take advantage of the availability of all individual normalized libraries and the cDNA catalogue to generate a number of tissue-specific and developmental-specific sub-libraries.

The plan is to utilize as a driver a mixture of in vitro synthesized RNA from all but one of the normalized library components of the cDNA catalogue, in a hybridization where the tracer will be single-stranded circles form the cDNA catalogue (which contains all libraries including that one missing in the driver) [see FIG. 4]. In other words, supercoiled plasmid DNA from each individual normalized library (except one) will be linearized and separately utilized as templates for in vitro synthesis of RNA. After annealing to the blocking oligonucleotide, and digestion with both RNAse H and RNAse-free DNAse, as detailed above, all synthesized RNAs (20–40 µg) will be pooled together and hybridized to trace amounts (0.1 µg) of single-stranded circles from the cDNA catalogue. If hybridization goes to completion, only-single stranded circles from the library missing in the driver should be found in the flow-through (HAP or vectrex-avidin) fraction. Once again, verification of tissue-specificity would be easily accomplished by single-pass sequencing.

For example applicants plan to use this system to isolate embryonic-specific cDNAs.

Similarly applicants will attempt to isolate brain (fetal, infant and adult), liver (fetal, infant and adult), spinal cord (adult), lung (infant), heart (infant), spleen (infant) and muscle (infant)-specific subtracted libraries. Applicants will sequence 100 clones from each subtracted library and applicants will estimate their complexities by colony hybridization experiments, as described above.

Applicants anticipate that such resources will prove valuable for many purposes, e.g. identification of novel tissue and temporal-specific transcripts, chromosomal localization of differentially expressed genes (by painting chromosomes with pools of clones from tissue-specific sub-libraries; since cDNA inserts are large in our libraries this should be straightforward by fluorescence in situ hybridization). Furthermore, the availability of this cDNA catalogue as a reference library should facilitate ongoing efforts for isolation of chromosome-specific cDNAs, large sequencing of cDNAs, and cloning of disease-causing genes. Methods for identification of transcribed sequences from genomic DNA, such as exon trapping (Duyk et al., 1990; Hamaguchi et al., 1992), exon amplification (Buckler et al., 1991), cDNA selection (Parimoo et al, 1991), and direct selection (Lovett et al., 1991; Morgan et al., 1992) should also benefit from this cDNA catalogue. "Exon amplification" and "exon trapping" are methods that take advantage of RNA splicing to capture expressed sequences from large regions of genomic DNA. "Direct selection" and "cDNA selection" utilize a genomic target DNA, a YAC clone for example, for hybrid selection of cDNAs. At the end either the small exons that were trapped or the short cDNA fragments that were selected need to be utilized to "fish" more informative cDNA clones from high quality cDNA libraries. Applicants also have developed a method for hybrid selection of cDNA clones (as single-stranded circles with filter immobilized genomic DNA, which applicants are utilizing to identify chromosome 13-specific cDNAs (Bonaldo et al., manuscript in preparation). However, to identify as many transcribed sequences as possible from any given region of DNA applicants would have to go through selections with a number of different libraries, as opposed to only one, if the cDNA catalogue were already available.

As mentioned before, applicants plan to make these resources available to all interested investigators. As an example, our infant brain library has been distributed to many institutions in the U.S.A. and abroad (Lawrence Livermore, Argonne Laboratories, Harvard Medical School, University of Colorado, NIH, University of Pennsylvania, Genethon (France), MRC (Cambridge) and Rijks University (The Netherlands).

Human Subjects 1 and 2. The fetal tissues required for this project will be obtained from voluntary pregnancy terminations. These terminations are usually by suction curettage. The products of conception are considered surgical pathology specimens (category 5 of exceptions) that are discarded after examination. Voluntary terminations are suitable for this project because the procedures are scheduled, the tissues are fresh, and genetic abnormalities are usually absent. Tissues will be obtained from the Short Stay Surgical Unit of the Presbyterian Hospital through the cooperation of members of the Departments of Obstetrics and Gynecology, and Pathology. Dr. Stephen Brown, who is both a member of our team and a faculty member in OBGYN, will serve as a liaison. All specimens will be identified by accession number, and no names of patients will be kept.

3. Since the tissues that applicants will collect are normally discarded pathological specimens, and no identification information will be retained, there will be no contact with the patients.

4, 5 and 6. The subjects are not exposed to any kind of potential risk by this study, because no additional procedures are carried out, and only the pathological material from non-viable products of conception will be used. The study does not involve persons under the age of 18 nor any drugs, medical devices or questionnaires.

References

1. Adams, M. D., et al. (1991). Complementary DNA sequencing: expressed sequence tags and human genome project. Science 252:1641–1656.
2. Adams, M. D., et al. (submitted for publication). Rapid cDNA Sequencing (Expressed Sequence Tags) from a Directionally Cloned Human Infant Brain cDNA Library.
3. Atschul, S. F., et al. (1990). Basic local alignment search tool. J. Mol. Biol. 215:403–419.
4. Bishop, J. O., et al. (1974). Nature 250:199–204.
5. Britten, R. J., et al. (1974). Analysis of repeating DNA sequences by reassociation. Meth. Enzymol. 29:363–441.
6. Buckler, A. J., et al. (1991). Exon amplification: a strategy to isolate mammalian genes based on RNA splicing. Proc. Natl. Acad. Sci. U.S.A. 88:4005–4009.
7. Davidson, E. H. and Britten, R. J. (1979). Science 204:1052–1059.

8. Dear, T. N., et al. (1991). Novel genes for potential ligand-binding proteins in subregions of the olfactory mucosa. EMBO J. 10(10):2813–2819.
9. Dear, T. N., et al. (1988). Differential expression of a novel gene, WDNM1, in nonmetastatic rat mammary adenocarcinoma cells. Cancer Res. 48:5203–5209.
10. Dower, W. J., et al. (1988). High Efficiency transformation of *E. coli* by high voltage electroporation. Nuc. Acids Res. 16(3);6127–6145.
11. Duguid, J. R., et al. (1988). Isolation of cDNAs of scrapie-modulated RNAs by subtractive hybridization of a cDNA library. Proc. Natl. Acad. Sci. U.S.A. 85:5738–5742.
12. Duyk, G. M., et al. (1990). A genetic screen to identify candidate transcribed sequences in cloned mammalian genomic DNA. Proc. Natl. Acad. Sci. U.S.A. 87:8995–8999.
13. Galau, G. A., et al. (1977). Arch. Biochem. Biophys. 179:584–599.
14. Hamaguchi, M., et al. (1992). Establishment of a highly sensitive and specific exon-trapping system. Proc. Natl. Acad. Sci. U.S.A. 89:9779–9783.
15. Hara, E., et al. (1991). Subtractive cDNA cloning using oligo(dt)30-latex and PCR: isolation of cDNA clones specific to undifferentiated human embryonal carcinoma cells. Nuc. Acids Res. 19(25): 7097–7104.
16. Huynh, T. V., et al. (1985). Constructing and Screening cDNA Libraries in λgt10 and λgt11. In "DNA Cloning Volume I" (ed. D. M. Glover), pp. 49–78. IRL Press Limited, England.
17. Khan, A. S., et al. (1992). Single pass sequencing and physical and genetic mapping of human brain cDNAs. Nature Gen. 2:180–185.
18. Kho, C-J and Zarbl, H. (1991). A rapid and efficient method for the generation of a subtracted cDNA library. Technique 3(2):58–63.
19. Klar, A., et al. (1992). F-Spondin: a gene expressed at high levels in the floor plate encodes a secreted protein that promotes neural cell adhesion and neurite extension. Cell 69:95–100.
20. Ko, M. S. H. (1990). An "equalized cDNA library" by the reassociation of short double-stranded cDNAs. Nuc. Acids Res. 18:5709.
21. Kornberg, A. and Baker, T. A. (1992). RNA-Directed DNA Polymerases: Reverse Transcriptases and Telomerase. In "DNA Replication", 2nd Edition, pp. 217–222. W. H. Freeman and Company, New York.
22. Krady, J. K., et al. (1990). Use of avidin-biotin subtractive hybridization to characterize mRNA common to neurons destroyed by the selective neurotoxicant trimethyltin. Mol. Brain Res. 7:287– 297.
23. Lee, S. W., et al. (1991). Positive selection of candidate tumor-suppressor genes by subtractive hybridization. Proc. Natl. Acad. Sci. U.S.A. 88:2825–2829.
24. Loros, J. J., et al. (1989). Molecular cloning of genes under control of the circadian clock in Neurospora. Science 243:385–388.
25. Lovett, M., et al. (1991). Direct selection: a method for isolation of cDNAs encoded by large genomic regions. Proc. Natl. Acad. Sci. U.S.A. 88:9628–9632.
26. Miller, F. D., et al. (1987). J. Neurosci. 7(8):2433–2444.
27. Morgan, J. G., et al. (1992). The selective isolation of novel cDNAs encoded by the regions surrounding the human interleukin 4 and 5 genes. Nuc. Acids Res. 20(19):5173–5179.
28. Owens, G. P., et al. (1991). Identification of mRNAs associated with programmed cell death in immature thymocytes. Mol. Cell. Biol. 11(8):4177–4188.
29. Parimoo, S., et al. (1991). cDNA selection: efficient PCR approach for the selection of cDNAs encoded in large chromosomal DNA fragments. Proc. Natl. Acad. Sci. U.S.A. 88:9623–9627.
30. Patanjali, S. R., et al. (1991). Construction of a uniform-abundance (normalized) cDNA library. Proc. Natl. Acad. Sci. U.S.A. 88:1943–1947.
31. Rubenstein, J. L. R., et al. (1990). Subtractive hybridization system using single-stranded phagemids with directional inserts. Nuc. Acids Res. 18(16):4833.
32. Sive, H. L. and St. John, T. (1988). A simple subtractive hybridization technique employing photoactivable biotin and phenol extraction. Nuc. Acids Res. 16(22):10937.
33. Smith, C. L., et al. (1987). Strategies for mapping and cloning macroregions of mammalian genomes. Methods in Enzimol. 151:461–489.
34. Swaroop, A., et al. (1991). A simple and efficient cDNA library subtraction procedure: isolation of human retina-specific cDNA clones. Nuc. Acids Res. 19(8):1954.
35. Sykes, D. E. and Weiser, M. M. (1992). The identification of genes specifically expressed in epithelial cells of the rat intestinal crypts. Differentiation 50:41–46.
36. Travis, G. H. and Sutcliffe, J. G. (1988). Proc. Natl. Acad. Sci. U.S.A. 85:1696–1700.
37. Travis, G. H. et al. (1987). Subtractive cloning of complementary DNAs and analysis of messenger RNAs with regional heterogeneous distributions in primate cortex. Neuropharmacol. 26(7B):845–854.
38. Weissman, S. M. (1987). Molecular genetic techniques for mapping the human genome. Mol. Biol. Med. 4:133–143.
39. Yancopoulos, G. D., et al. (1990). Isolation of coordinately regulated genes that are expressed in discrete stages of B-cell development. Proc. Natl. Acad. Sci. U.S.A. 87:5759–5763.
40. Zabarovsky, E. R. and Weinberg, G. (1990). High efficiency electroporation of ligated DNA into bacteria. Nuc. Acids Res. 18(19):5912.

SECOND SERIES OF EXPERIMENTS

INTRODUCTION

Two strategies have been proposed to normalize cDNA libraries, the "genomic" and the "kinetic" approaches (Weissman, 1987). The genomic approach is based on hybridization of saturating amounts of cDNA to genomic DNA. The frequency of each hybridized cDNA in the resulting normalized library would be proportional to that of each corresponding gene in genomic DNA. The requirement that even the rarest cDNAs be present at saturating levels, however, makes this approach technically cumbersome. The alternative is the kinetic approach: if cDNA reannealing follows second-order kinetics, rarer species anneal less rapidly and the remaining single-stranded fraction of cDNA becomes progressively more normalized during the course of the hybridization (Galau et al., 1977). Specific loss of any species of cDNA, regardless of its abundance, does not occur at any Cot value.

The kinetic approach has been successfully utilized to normalize cDNA libraries by two independent groups (Ko, 1990; Patanjali et al., 1991).

Ko (1990) constructed a normalized mouse cDNA library by a scheme involving ligation of sheared cDNAs (200–400 bp) to a linker-primer adaptor, and one to three cycles of: (i) PCR amplification, (ii) denaturation-reassociation, and (iii) purification of the remaining single stranded cDNAs by hydroxyapatite (HAP) column chromatography. The resulting single-stranded material was PCR amplified, digested at a site present in the linker-primer sequences. Colony hybridization with eight probes of different abundances showed a reduction in abundance variation from at least 20,000 fold in the original library to 40-fold in the library constructed after three cycles of normalization.

Patanjali et al (1991) reported the utilization of a similar strategy to normalize a human adult thymus cDNA fragments into γgt10, (ii) PCR amplification of cloned cDNAs, (iii) denaturation and reassociation to moderate Cot, (iv) separation of single-strands by HAP Chromatography, (v) PCR amplification of HAP-flow-through single-stranded cDNA and (vi) cloning into γgt10. This procedure differs from Ko's (1990) in that both coding and non coding sequences are represented in the final library. The starting cDNA fragments were size selected [400–1,600 bp] to minimize length dependent differential PCR amplification.

As discussed by Ko (1990), coding sequences from different members of a gene family are likely to cross-hybridize during the reassociation reaction. Since some gene family members may be much more prevalent than others, there is a potential risk that the least frequent member be eliminated from the final library. 3' untranslated sequences of mRNAs, on the other hand, are usually unique to individual transcripts. For this reason Ko (1990) utilized short cDNAs for the reassociation reaction, and forced the cloning of those fragments containing 3' untranslated sequences only.

Applicants have developed a method for normalization of directionally cloned cDNA libraries constructed in phagemid vectors, which is also based on the kinetic principle. Briefly, the method involves annealing of the library in the form of single-stranded circles to a NotI oligo (dT)18 primer, and controlled extensions (200–250 nt) with Klenow in the presence of dNTPs and ddNTPs to generate a cDNA library in the form of partially duplex circular DNA molecules that can then be normalized by the kinetic approach, i.e melting and reannealing to moderate Cot, and purification of the unreassociated single-stranded circles (normalized library) by hydroxyapatite column chromatography. Since the unreassociated material (HAP-flow-through) consists of already cloned cDNAs in the form of single-stranded circles, they can be readily electroporated into bacteria and propagated under appropriate antibiotic selection. This is in contrast to the alternative methods, according to which at the end of the reassociation reaction the remaining single stranded cDNAs need to be amplified by PCR and cloned.

Because this method does not require any cycle of cDNA amplification by the polymerase chain reaction, there are no length constraints on the cDNAs, and the normalized library consists of cDNA clones that have large size inserts (average of 1.7 kb).

It is noteworthy that although both coding and non-coding exons are represented in the normalized library, only 3' non-coding sequences participate in the reassociation reaction, thus minimizing the risk of eliminating low copy cDNAs due to cross hybridization between their coding sequences and those of other family members that are represented at a higher frequency in the starting cDNA library.

Here, applicants report the utilization of this method to construct a normalized human infant brain cDNA library in which the frequency of each clone is within a narrow range.

METHOD

Preparation of a directionally cloned human brain cDNA library

Total cellular RNA from a 73 day old post-natal female human brain was extracted according to a modification (Puissant and Houdebine, 1990) of the procedure described by Chomczynski & Sacchi (1987), and poly (A)+RNA was purified by standard procedures (Sambrook et al., 1989). A detailed description of the protocol utilized for construction of this human infant brain cDNA library has been provided elsewhere (Soares, in press).

Briefly, a Not I (dT)18 oligonucleotide [5'AACTGGAA-GAATTCGCGGCCG.SAGGAA(T)18, SEQ ID No. 4] was utilized as primer for first strand cDNA synthesis. After ligation to Hind III adapters, the CDNAs were digested with Not I (after appropriate size selections) and directionally cloned into the Hind III and Not I sites of a plasmid vector (lafmid BA) derived from pEMEL. The polylinker of the lafmid BA vector contains the following restriction sites: 5' Hind III-Bam HI-Not I-Eco RI 3'. The vector has an fl origin for production of single-stranded circles upon super infection with a helper phage. Single-stranded library DNA represents the message (mRNA-like) strand and therefore all single-stranded circles contain a short polyadenylic acid tail at their 3' end. The high representation of mRNA sequences in this library has been firmly documented by single pass sequencing of over 2,000 randomly picked clones (Khan et al., 1992; Adams et al., in press). The main features of this library are: (1) average cDNA size of 1.6 kb; (2) short polyadenylic acid tails; (3) non recombinants account for less than <0.1% of the clones; (4) chimeric cDNA clones have not been identified yet.

Propagation of cDNA libraries in the form of single-stranded circles

1–10 ng supercoiled plasmid DNA representing the entire library was electroporated into dH5oF' (electroporation efficiency of 5×10 9 c.f.u/mg supercoiled plasmid), grown at 37° C. for 1 h and then propagated under ampicillin selection overnight. The culture was then diluted 100 fold with fresh medium and grown in the presence of 0.2% glucose under ampicillin selection to A600-0.2. At this time the culture was superinfected with a 10–20 fold excess of helper phage (R408 or M13K07) and grown for only 4 h. Single-stranded DNA was then prepared according to standard protocol.

Single stranded circles were purified from any residual double-stranded plasmid (RF) contaminant as follows: 20 mg single stranded library DNA in 2 mls 0.12M PB-1% SDS- 10 mM EDTA were passed through 0.4 g HAP-60° C., preequilibrated with 0.12M PB-10 mM EDTA-1% SDS, the column was washed with 6 mls loading buffer and the combined HAP-flow-through (single-stranded circles in a total of 8 mls) was extracted twice with 30 mls H2O-saturated sec-butanol, once with 30 mls dry sec-butanol, once with 30 mls dry sec-butanol, and once with 20 mls of H2O saturated ether. The ether was blown off, and the sample was desalted by passage through a Nensorb column (DuPont) according to the manufacturer's instructions. [It should be noted that single-stranded circles are very sensitive to high temperatures (electroporation efficiencies of single-stranded circles drop very dramatically upon boiling, for example). However, a quick (1–2 min per passage) purification through a 60° C.-HAP column does not damage single-stranded circles in our hands.

HAP-purified single-stranded DNA was then purified from any residual amount of tRNA and from most of the helper phage DNA by agarose gel electrophoresis. The agarose gel slice containing the single-stranded library DNA smear was casted into a low melting point agarose gel, the current was reversed and the DNA was electrophoresed backwards (just to sharpen the smear) until it entered the low melt agarose gel. The low melt gel slice containing the library DNA was digested with agarose (NEE) and the single-stranded circles were ethanol precipitated. This gel purification step proved to be necessary to avoid undesirable internal priming events promoted by small RNA oligonucleotides (breakdown products from RNAse A digestion of tRNAs). The single-stranded DNA was never exposed to U.V. light [A small fraction of it was run on a separate lane, which was exposed to U.V., and served as a reference; this DNA was not used].

Applicants have performed control colony hybridization experiments to show that the frequency of several of the abundant clones (α-tubuli, elongation factor 1α, -tubuli and myelin basic protein) was absolutely identical in both the starting double-stranded library and in the library in the form of single-stranded circles. Thus, if prepared under the conditions described above, the library in the form of single-stranded circles is perfectly representative of the starting library.

cDNA library Normalization

See FIG. 1. for a schematic representation of the normalization procedure.

a) 0.6 pmoles of a ½ Not I-(dT)15 oligonucleotide [5' GGCCGCAGGAA(T)15 3', SEQ ID Nos. 5 and 6] were added to 0.3 pmoles of single-stranded circles (library DNA) in a 10 ul reaction containing 30 mM Tris pH7.5-50 mM NaCl- 15 mM MgCl2-1 mM DTT-0.1 mM each deoxynucleotide (dA,dC,dT, and dG)-2.5 mM each dideoxynucleotide (ddA,ddC and ddG; but no ddT)-and a trace of α32pdCTP. The mixture was first incubated for 5 min at 60° C., and then for 15 min at 50° C. (annealing temperature). At that time, the temperature was lowered down to 37° C., 5 units of Klenow enzyme were added and the reaction remained at 37° C. for 30 min. 15 such reactions were carried out in parallel. The end product of these reactions were partial duplex circles. The size distribution of the synthesized strand was rather narrow (200 nt±20; see FIG. 2 lane 3). [Since 3' non coding exons are usually larger than 300 nt (average of 750 nt in brain), the vast majority of the synthesized material should correspond to 3' untranslated sequences]. [Klenow was the only polymerase among several tested (T4 DNA Polymerase, Vent DNA Polymerase, Reverse Transcriptase and T7 DNA Polymerase) to generate extension products with such a narrow size distribution]. The next step was to purify these partially duplex circular molecules from any remaining (unprimed) single-stranded circles by HAP chromatography c) All 15 reactions were pooled together and stopped with EDTA (20 mM f.c.). The sample was extracted with phenol+Sevag, and phosphate buffer (PB) was added to a final concentration of 0.12M. At this time 2 mls of 60° C.-prewarmed 0.12M PB-10 mM EDTA-1% SDS containing 50 ug denatured sonicated salmon sperm DNA were added to the sample and this mixture was passed through a hydroxyapatite (HAP) column at 60° C. The column (0.4 g HAP, about 1 ml bed volume) had been pre-equilibrated with 0.12M PB. After a wash with 6 mls of 0.12M PB-10 mM EDTA-1% SDS, the partial duplex circles (HAP-bound) were eluted off the column with 6 mls of 0.4M PB-10 mN EDTA- 1% SDS. 14 mls H2O containing 50 ug denatured sonicated salmon sperm DNA were added to this eluate to lower the PB concentration down to 0.12M PB f.c., the column was reequilibrated with 0.12M PB-10 mM EDTA-1% SDS and the sample was passed through HAP again. [This is necessary because a small fraction of single-stranded DNA can bind, non specifically to HAP; this background is of the order of 0.1%; by passing it through twice this background becomes irrelevant]. The column was washed with 6 mls 0.12M PB-10 mM EDTA-1% SDS and the partially duplex circles (HAP-bound) was eluted with 6 mls 0.4M PB-10 mM EDTA-1% SDS.

d) The eluate was desalted by passage through a Nensorb column (DuPont), after a few extractions with H2O-saturated and dried sedbutanol. DNA was eluted off the Nensorb column with 1 ml 20% n-propanol in H2O, vacuum-dried for 30 min, (at this point an aliquot of the material was applied on a 6% sequencing gel; see FIG. 2) and ethanol precipitated.

e) The DNA pellet (112.5 ng) was resuspend in 2.5 ul formamide and heated for 3 min at 80° C. under a drop of mineral oil. 1 ul 5 ug/ul oligo-(dT) 25–30, 0.5 ul 1 ug/ul ½ Not-(dT)15 oligonucleotide, 0.5 ul 5M NaCl, and 0.5 ul 0.1M Tris-0.1M EDTA (total 5 ul) were added and the mixture was incubated at 42° C. [oligo-(dT) 25–30 and ½ Not-(dT)15 oligonucleotides were present to block the polyadenylic acid tails]. 0.5 ul aliquots were taken at 13 h (Cot-8) and 84 h (Cot-51.5). The best normalization results (see Table 1) were obtained after 13 h incubation.

f) In the next step, the remaining (normalized) single stranded circles were separated from the (reassociated) partially double-stranded circular molecules by HAP chromatography.

To 0.5 ul of the hybridization mixture, applicants added 5 ug of denatured sonicated salmon sperm DNA+2 mls of 60° C. prewarmed 0.12M PB-10 mM EDTA-1% SDS and the sample was passed through 0.4 g HAP. The column was washed with 6 mls 0.12M PB-10 mM EDTA-1% SDS and the HAP-flow-through (containing the normalized single-stranded circles) was passed through a second (fresh) HAP column just to minimize the chance that any residual amount of partially double-stranded molecules escaped from binding through some undetected small channel in the column; by passing it through a fresh column this potential problem was eliminated. The column was washed with 6 mls 0.12M PB-10 mM EDTA-1% SDS and the flow-through material (normalized single-stranded circles) was desalted through a Nensorb column as described above. HAP-bound DNA from the first column was also purified.

g) At this point, one can either directly electroporate the single-stranded circles (HAP-flow-through) into competent DH10B bacteria, or one may convert them into partially double-stranded circles (by primed extension) in order to improve their electroporation efficiencies by 50–100 fold. Such extensions can be primed with random hexamers, or with the M13 Universal primer.

After 1 h at 37° C., an aliquot of the culture (10 ul out of 100 mls) was plated on an LB agar plate containing ampicillin for determination of total number of transformants, ampicillin was added to the culture to a final concentration of 75 ug/ml, and the bacteria were propagated till the culture reached mid-log phase. Supercoiled plasmid DNA (normalized library) was extracted by alkaline lysis and purified over a Qiagen midi-size column. Applicants obtained 2.5 million transformants from the 0.5 ul of hybridization mixture that were processed.

Colony hybridization

Colony hybridizations were done essentially as described (Grunstein). For best results while making replica filters with nylon membranes (GeneScreenPlus) the plate with bacteria should be kept at 4° C. for 1–2 hs, the master filter (first to be pulled off the plate) should not be prewetted whereas the second filter (to be pulled off the master filter) should be prewetted on an empty agar plate. Hybridization and washing conditions were as described before (Zeitlin & Efstratiadis).

DNA sequencing

Double-stranded plasmid DNA templates were prepared using MagidPrep (Promega) or Qiagen columns as described by the manufacturer's instructions.

DNA sequencing was performed by the cycle sequencing protocol (ABI) according to the manufacturer's instructions, using an automated ABI370A DNA Sequencer.

Database searches

Blastn and Blastx database searches were performed at the NCBI using the BLAST network service. [Altschul, Stephen F., Warren Gish, Webb Miller, Eugene W. Myers, and David J. Lipman (1990). Basic local alignment search tool. J. Mol. Biol.215:403–410.]

RESULTS

The efficiency of normalization was assessed by three criteria: (a) colony hybridization of both starting and normalized libraries with a number of cDNA probes representing mRNAs that occur in the starting library at a wide range of frequencies (Table 1), (b) screening of the normalized library with a number of cDNA probes derived from clones that were randomly pricked from the normalized library itself, and (c) by single-pass sequencing (from both the 5 and 3' ends) of approximately 200 cDNA clones (over 100 kb total sequence). Altogether these results strongly indicate that normalization was successful.

The cDNA probes that were utilized for screening of both starting and normalized libraries (Table 1) can be arbitrarily grouped into 3 classes: prevalent, with frequencies in the starting library ranging from 0.5–5%, intermediate (0.05–0.5%) and complex (<0.05%). Normalization reduced the frequency of the prevalent cDNAs by about 10–100 fold (with the exception of mitochondrial 16S rRNA, see below), that of the intermediates by 3–16 fold, whereas the frequency of the cDNAs from the complex class remained practically the same. The difference in frequency between the most and the least abundant clones in the starting library (elongation factor 1-α at 4.6% and cDNA#250-1 at 0.008%) was reduced from 575 down to 3 with the normalization procedure.

As described in the method's section, an aliquot of the hybridization mixture was passed over HAP to separate the remaining single-stranded circles (HAP-flow-through, normalized library) from the reassociated partially duplex molecules (HAP-bound). Both HAP-flow-through and HAP-bound fractions were processed so that applicants could verify that the frequency of an abundant cDNA was lowered in the normalized library (HAP-flow-through), because it reassociated fast and therefore it ended up in the HAP-bound fraction. Indeed, the frequency of two of the most abundant clones in the starting library [elongation factor 1-α (4.6%) and α-tubuli (4%) was reduced 100 fold (0.4% and 0.5%, respectively) in the HAP-flow-through fraction (normalized library) but remained high (3.7% and 6%, respectively) in the HAP-bound-fraction (the reassociated material), further documenting the efficacy of the kinetic approach to normalize cDNA libraries].

If a library is normalized, one would expect that any randomly picked clone would be represented within a narrow range of frequencies. To test this hypothesis, eight clones were randomly picked from the normalized library, and probes made from them were used to screen the normalized library itself (Table 2). The frequency of all eight cDNAs fell within a 13-fold range, varying from 0.003% to 0.04%. Overall, based on colony hybridization experiments with 27 probes (Tables 1 and 2), the frequency variation in the normalized library is of the order of 50 fold (the 16S mitochondrial rRNA was excluded from this analysis, see below).

To further document that normalization was successful, 190 cDNA clones were randomly picked from the normalized and single-pass sequenced from both ends (Table 3). Database searches of the public nucleic acid and protein databases revealed that 69% (131/190) of the clones correspond to novel brain expressed sequences: no matches could be identified in the public nucleic acid or protein databases to either their 3' or 5' end sequences. 19% (25/131) of those contained repetitive elements (mostly Alu) in either their 3' or 5' ends. 25% (48/190) of the clones had matches to known human sequences, 50% (24/48) of which to "ESTs to unknown genes". 6% (12/190) of the clones were putatively identified based on similarities to known sequences of other organisms, (mainly Rodent, Drosophilia, yeast or C.elegans). Among those putative gene identifications are an homologue of the yeast prmRNA splicing factor RNA helicase PRP22, a homologue of a Drosophila GTP-binding protein, the homologue of the Drosophila puff specific protein Bx42, and CDNAs similar to the Streptomyces exfoliatus-20 beta-Hydroxysteroid dehydrogenase, yeast hypothetical 43.3 kd protein, Chines hamster DHFR-coamplified protein mRNA, and Rat plasma membrane Ca2+ ATPase-isoform 2 mRNA.

1,633 randomly picked clones from this same infant brain library (prior to normalization) have been single-passed sequenced (mostly from their 5' ends) [Adams et al., in press]. 37% of the clones were putatively identified by database searched, and 63% corresponded to sequences with not matches in the databases.

Applicants have performed Fasta searches of all 5' sequences obtained from those 190 clones that were randomly picked from the normalized library against 1624 sequences (kindly provided by M. Adams, TIGR) that were generated by random picking of clones from the same infant brain library prior to normalization. Only 8% (15/190) of the clones randomly picked from the normalized library had already been identified within those 1624 sequences derived from the non normalized library. Three of these matches corresponded to overlapping clones (cDNA clones of different lengths presumably derived from the same mRNA) rather than to the same clone. Five of these 15 clones corresponded to sequences not previously identified (no matches in the public databases). Five of them corresponded to already identified "ESTs to unknown genes". Five of them corresponded to known human sequences: mitochondrial 16S rRNA (3 clones), a human cDNA similar to mouse cysteine-rich protein and a human 23 Kd highly basic protein.

Similarly, 178 sequences were randomly selected from the 1624 ESTs derived from the non normalized library, and Fasta searched against the remainder 1446 sequences. 31% (55/178) of those had matches among the 1446 ESTs, i.e. they were represented at least twice in the original pool of 1624 sequences. Many hits were found to all those cDNA clones representing the prevalent mRNAs such as elongation factor 1-α, elongation factor 1y, α-tubuli, B-tubuli, y-actin and myelin basic protein.

DISCUSSION a) The method is advantageous because there is no PCR involved and because only 3' non coding sequences participate in the reassociation reaction.

b) Internal priming is a potential problem, and it can explain how come the frequency of 16S mitochondrial rRNA did not go down as it should have after normalization. Applicants have obtained sequence data from a number of 16S clones from the starting and normalized libraries. All clones in the starting library are full length or near full length. Most 16S rRNA clones in the normalized library are truncated versions generated by internal priming. The interpretation is that the extension products of both the full length and truncated circle templates can reassociate to the full length circles but only the extension products derived from the truncated version can reassociate to the truncated circle. Thus, there is a chance that a full length circle would reassociate to two extension products (one derived from the full length template and another derived from the truncated version). If that happens the truncated template will not have any extension product to reassociate with and therefore will be present in the normalized library. Applicants will discuss the utilization of a different primer to prime 1st strand cDNA synthesis which will help to minimize this problem.

c) Another important item to discuss is the fact that the frequency of repetitive sequences does not go down with normalization. This was also observed by the other groups and it is a very fortune fact. It would be undesirable if the frequency would go down because that would indicate that rare cDNAs that happened to have a repeat in their 3' non coding region could potentially be eliminated with normalization. Thus, it is an advantage that applicants do not see that happen. The reason why that does not happen is because double strand DNA will only bind to HAP if it is at least 100 bp long and if does not have mismatches. In other words, it takes about 100 bp of a perfect duplex to bind to HAP under our conditions. Repetitive sequences are grouped into families and the sequence divergence among their members is high enough so that the hybrids that are formed upon reassociation will be imperfect and therefore will escape binding to HAP.

d) In Ko's method, both coding and non coding fragments are present during reassociation. However, after the final digestion and directional cloning steps only the 3' non coding fragments remain in the normalized library. Ko's rationale for constructing a normalized library consisting exclusively of 3' non coding sequences was the following. The 3' non coding terminal exon of a mRNA is almost always unique to that transcript. Thus, during the reassociation step, each 3' non coding sequence is expected to only reanneal to its very complementary strand. In contrast, coding exons may be conserved among members of a gene family, some of which might be less represented than others in a given tissue. Thus, during reassociation, the most frequent of such coding sequences might cross-hybridize to a related, but divergent, complementary strand from a less prevalent family member, which could result in the elimination of the rarer family member from the normalized library.

What is claimed is:

1. A method to normalize a directional cDNA library comprising cDNA clones constructed in a vector that allows propagation in single-stranded circle form comprising:

(a) propagating the directional cDNA library in single-stranded circles;

(b) annealing the single-stranded circles to an appropriate primer and performing controlled extension reactions with an appropriate polymerase in the presence of an appropriate ratio between dideoxynucleotide triphosphates and deoxynucleotide triphosphates to generate fragments complementary to the 3' noncoding sequence of the single-stranded circles in the library to produce partial duplexes;

(c) purifying the partial duplexes;

(d) melting and reassociating the purified partial duplexes to appropriate Cot; and (e) purifying unassociated single-stranded circles, thereby generating a normalized cDNA library.

2. A method of claim 1, wherein the directional cDNA library is generated by using a primer having a rare restriction enzyme recognition site for the first strand cDNA synthesis, upstream of the oligodT stretch.

3. A method of claim 2, wherein the rare restriction enzyme recognition site is a Not I or Pac I site.

4. A method of claim 1, wherein the controlled extensions are performed with Klenow.

5. A method of claim 4, wherein the controlled extension are performed in the presence of a 25 fold excess of dideoxynucleotide triphosphates containing dideoxyadenosine triphosphate, dideoxycytidine triphosphate and dideoxyguanosine triphosphate over deoxynucleotide triphosphates including deoxyadenosine triphosphate, deoxycytidine triphosphate, deoxyguanosine triphosphate and deoxythymidine triphosphate.

6. A method of claim 1, wherein the cDNA clones with the fragments and the ones without the fragments are separated by hydroxyapatite column chromatography.

7. A method of claim 1, further comprising introducing the unassociated single-stranded circles into host cells.

8. A method of claim 7, further comprising conversion of the single-stranded circles into double-stranded DNA circles before the introduction into the hosts.

* * * * *